United States Patent
Beard et al.

(10) Patent No.: US 7,458,266 B2
(45) Date of Patent: Dec. 2, 2008

(54) METHOD AND APPARATUS FOR DETECTING A LOAD CHANGE UPON A STRUCTURE AND ANALYZING CHARACTERISTICS OF RESULTING DAMAGE

(75) Inventors: Shawn J. Beard, Livermore, CA (US); Xinlin Qing, Cupertino, CA (US); Hian Leng Chan, Cupertino, CA (US); Chang Zhang, Santa Clara, CA (US); Fuo-Kuo Chang, Stanford, CA (US)

(73) Assignee: Samsung Electronics Co. Ltd., Gyeonggi-do (KR)

( * ) Notice: Subject to any disclaimer, the term of this patent is extended or adjusted under 35 U.S.C. 154(b) by 399 days.

(21) Appl. No.: 11/060,650

(22) Filed: Feb. 16, 2005

(65) Prior Publication Data
US 2006/0079747 A1    Apr. 13, 2006

Related U.S. Application Data

(60) Provisional application No. 60/613,825, filed on Sep. 27, 2004.

(51) Int. Cl.
*G01N 29/04*    (2006.01)
*G01B 17/00*    (2006.01)

(52) U.S. Cl. .............................. 73/579; 73/789; 73/801; 702/39

(58) Field of Classification Search ............ 73/862.046, 73/760, 767, 772, 862.041, 587, 588, 579, 73/768, 789, 799, 801, 802, 803
See application file for complete search history.

(56) References Cited

U.S. PATENT DOCUMENTS

| | | |
|---|---|---|
| 3,713,127 A | 1/1973 | Keledy et al. |
| 3,822,586 A | 7/1974 | Pollock |
| 3,858,439 A | 1/1975 | Nakamura |

(Continued)

FOREIGN PATENT DOCUMENTS

DE    4237404    5/1994

(Continued)

OTHER PUBLICATIONS

Roh, Youn-Seo, et al., "*Effect of Impact Damage on Lamb Wave Propagation in Laminated Composites*" Department of Aeronautics and Astronautics, Stanford University, Stanford, CA 94305 (1995) pp. 1-12.

(Continued)

*Primary Examiner*—Hezron Williams
*Assistant Examiner*—Jacques Saint-Surin
(74) *Attorney, Agent, or Firm*—MacPherson Kwok Chen & Heid LLP

(57) ABSTRACT

A sensor network is attached to a structure and employed to detect and analyze load changes. The sensor network has transducers, capable of acting as both passive sensors and active actuators, integrated within it. In a passive mode, the transducers detect load changes upon the structure, such as impacts. Upon detection of a load change, the transducers are engaged in an active mode to actively scan the impact area to determine the location and size of any resulting damage region. In this manner, passive and active systems are integrated within a single, convenient layer that possesses the best features of both active systems and passive systems.

41 Claims, 15 Drawing Sheets

U.S. PATENT DOCUMENTS

| | | | |
|---|---|---|---|
| 3,924,456 A | 12/1975 | Vahaviolos | |
| 3,956,731 A | 5/1976 | Lewis, Jr. | |
| 4,006,625 A | 2/1977 | Davis | |
| 4,107,981 A | 8/1978 | Kanagawa et al. | |
| 5,176,032 A | 1/1993 | Holroyd et al. | |
| 5,195,046 A | 3/1993 | Gerardi et al. | |
| 5,298,964 A * | 3/1994 | Nelson et al. | 356/33 |
| 5,714,687 A | 2/1998 | Dunegan | |
| 5,774,376 A | 6/1998 | Manning | |
| 5,814,729 A * | 9/1998 | Wu et al. | 73/588 |
| 6,006,163 A | 12/1999 | Lichtenwalner et al. | |
| 6,065,342 A | 5/2000 | Kerr et al. | |
| 6,170,334 B1 * | 1/2001 | Paulson | 73/587 |
| 6,252,334 B1 | 6/2001 | Nye et al. | |
| 6,370,964 B1 | 4/2002 | Chang et al. | |
| 6,399,939 B1 | 6/2002 | Sundaresan et al. | |
| 6,418,384 B1 | 7/2002 | Rothea et al. | |
| 6,529,127 B2 | 3/2003 | Townsend et al. | |
| 6,691,007 B2 | 2/2004 | Haugse et al. | |
| 6,693,548 B2 | 2/2004 | Boyce et al. | |
| 6,768,312 B2 | 7/2004 | Sun et al. | |
| 6,826,982 B2 | 12/2004 | O'Brien et al. | |
| 7,075,424 B1 | 7/2006 | Sundaresan | |
| 7,103,507 B2 | 9/2006 | Gorinevsky | |
| 7,117,742 B2 * | 10/2006 | Kim | 73/587 |
| 7,118,990 B1 | 10/2006 | Xu et al. | |
| 7,201,035 B2 | 4/2007 | Sunshine | |
| 7,246,521 B2 * | 7/2007 | Kim | 73/587 |
| 2001/0047691 A1 | 12/2001 | Dzenis | |
| 2002/0154029 A1 | 10/2002 | Watters et al. | |
| 2003/0164700 A1 | 9/2003 | Goldfine et al. | |
| 2004/0002815 A1 | 1/2004 | Ishzaki et al. | |
| 2004/0032013 A1 | 2/2004 | Cobbley et al. | |
| 2004/0163478 A1 | 8/2004 | Xu et al. | |
| 2005/0072249 A1 | 4/2005 | Maeda et al. | |
| 2006/0042396 A1 | 3/2006 | Qing et al. | |
| 2006/0149449 A1 | 7/2006 | Baur et al. | |
| 2006/0154398 A1 | 7/2006 | Qing et al. | |
| 2006/0179949 A1 | 8/2006 | Kim | |
| 2006/0283266 A1 | 12/2006 | Qing et al. | |
| 2007/0018083 A1 | 1/2007 | Kumar et al. | |

FOREIGN PATENT DOCUMENTS

| | | |
|---|---|---|
| DE | 1983561 | 2/2000 |
| DE | 10217031 | 10/2003 |

OTHER PUBLICATIONS

Keilers, Charles Henry Jr., "*Damage identification in Composites Using Built-in Piezoelectrics: A Dissertation Submitted to the Department of Aeronautics and Astronautics and the Committee on Graduate Studies of Stanford University in Partial Fulfillment of the Requirements for the Degree of Doctor of Philosophy*", pp. 1-111 (Jun. 1993).

Chang, Fu-Kuo, "*Built-in Damage Diagnostics for Composite Structures*" Department of Aeronautics and Astronautics, Stanford University, Stanford, CA 94305 (1995).

Roh,Youn-Seo, "*Built-in Diagnostics for Identifying an Anomaly in Plates Using Wave Scattering*", UMI Microform 9924496, UMI Company, Ann Arbor, MI, (1999) pp. iv-88.

* cited by examiner

METHOD AND APPARATUS FOR DETECTING A LOAD CHANGE UPON A STRUCTURE AND ANALYZING CHARACTERISTICS OF RESULTING DAMAGE

BACKGROUND OF THE INVENTION

This application claims the benefit of U.S. Provisional Patent Application No. 60/613,825, filed on Sep. 27, 2004, which is incorporated herein by reference in its entirety.

BRIEF DESCRIPTION OF THE INVENTION

The present invention relates generally to structural health monitoring. More specifically, the present invention relates to the detection of load changes upon a structure, and the analysis of characteristics of any resulting damage.

BACKGROUND OF THE INVENTION

The diagnostics and monitoring of structures, such as that carried out in the structural health monitoring field, are often accomplished by employing arrays of sensing elements. While many advances have been made, the field continues to be challenged by an increased need to develop "smart" systems. For example, purely passive systems exist for detecting impacts and other load changes. However, these systems often do little more than detect the presence of such load changes, with any diagnosis or further analysis being left to other systems.

In contrast, purely active systems exist that are capable of querying a structure to determine its dynamic characteristics, but these active systems also suffer from their own drawbacks. For instance, active systems must constantly query the structure, resulting in wasted energy and expense when they are not needed. It is therefore desirable to combine active and passive systems in structural health monitoring, so as to simultaneously bring forth the advantages of both systems.

Furthermore, because each of these systems often requires large numbers of sensors in order to be effective, structures often must have a variety of sensing elements placed at various locations. Because individual sensing elements must often be placed separately, affixing a large array of such sensing elements can be tedious and time consuming. In addition, as each individual sensing element can require one or, commonly, multiple wires, large arrays of sensing elements can require a large number of individual wires, which may be difficult to handle and keep track of. The securing of such large numbers of wires can often be painstaking and time consuming, as well. It is therefore further desirable to combine active and passive sensors, and their wires, together in such a manner that the abovementioned difficulties are avoided, or at least reduced.

SUMMARY OF THE INVENTION

The invention can be implemented in numerous ways, including as a method, system, device, apparatus, or computer readable medium. Several embodiments of the invention are discussed below.

As a structural health monitoring system, one embodiment of the invention comprises a plurality of passive sensors coupled to a structure, a plurality of actuators coupled to the structure, and a controller. The controller is in electrical communication with the plurality of passive sensors and the plurality of actuators. It is also configured to receive from the plurality of passive sensors an indication of a load change generating a damage region on a structure, the damage region having a location and a size. The controller is further configured to direct the plurality of actuators to transmit stress waves through the structure so as to determine the location and the size of the damage region.

As a method of analyzing a damage region of a structure, another embodiment of the invention comprises receiving a first set of stress waves generated by a load change upon a structure, the load change also generating a damage region on a structure, the damage region having a location and a size. In response to the receiving, the method also includes transmitting a second set of stress waves through the structure so as to facilitate a determination of the location and the size of the damage region.

As a computer readable memory to direct a computer to function in a specified manner, another embodiment of the invention comprises a first module to receive a first set of stress waves generated by a load change upon a structure, the load change also generating a damage region on a structure, the damage region having a location and a size. Also included is a second module to transmit, in response to the receiving, a second set of stress waves through the structure so as to facilitate a determination of the location and the size of the damage region.

As a structural health monitoring system, another embodiment of the invention comprises a plurality of passive sensors configured to facilitate the analysis of a structure, and a plurality of actuators configured to facilitate the analysis of the structure. Also included are switches having first configurations establishing electrical connections with the plurality of passive sensors and second configurations establishing electrical connections with the plurality of actuators. The system also includes a controller in electrical communication with the switches. The controller is configured to toggle the switches to the first configurations so as to receive from the plurality of passive sensors an indication of a load change generating a damage region on a structure, and to the second configurations so as to direct the plurality of actuators to transmit stress waves through the structure.

Other aspects and advantages of the invention will become apparent from the following detailed description taken in conjunction with the accompanying drawings which illustrate, by way of example, the principles of the invention.

BRIEF DESCRIPTION OF THE DRAWINGS

The invention, together with further objects and advantages thereof, may best be understood by reference to the following description taken in conjunction with the accompanying drawings in which.

Like reference numerals refer to corresponding parts throughout the drawings. Also, it is understood that the depictions in the figures are diagrammatic and not necessarily to scale.

DETAILED DESCRIPTION OF EMBODIMENTS OF THE INVENTION

In one embodiment of the invention, a sensor network is attached to a structure and employed to detect and analyze load changes. The sensor network has transducers, capable of acting as both passive sensors and active actuators, integrated within it. In a passive mode, the transducers detect load changes upon the structure, such as impacts. Upon detection of a load change, the transducers are engaged in an active mode to actively scan the impact area to determine the location and size of any resulting damage region. In this manner, passive and active systems are integrated within a single, convenient layer that possesses the best features of both active systems and passive systems.

Figure 1A:
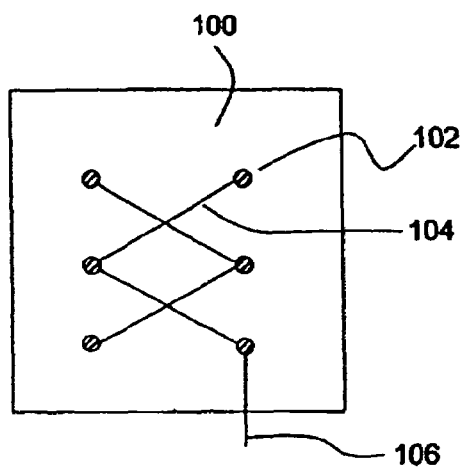
FIG. 1A illustrates a top view of a sensing layer manufactured in accordance with embodiments of the present invention.

For ease of installation, the sensor network can be placed on a flexible dielectric substrate to form a diagnostic layer. FIG. 1A illustrates such a flexible diagnostic layer for use in accordance with embodiments of the present invention. A diagnostic layer 100 is shown, which contains an array of transducers 102. As above, the transducers 102 can act as sensors capable of receiving signals used in structural health monitoring such as stress waves, and also as actuators capable of generating vibration, and are connected to conductive traces 104. The traces 104 connect (or interconnect, if necessary) transducers 102 to one or more output leads 106 configured for connection to a processor or other device capable of analyzing the data derived from the sensors 102. Accordingly, the transducers 102 can both passively generate electrical signals in response to stress waves, and actively transmit stress waves when a voltage is applied to them.

The diagnostic layer 100 and its operation are further described in U.S. Pat. No. 6,370,964 to Chang et al., which is hereby incorporated by reference in its entirety and for all purposes. Construction of the diagnostic layer 100 is also explained in U.S. patent application Ser. No. 10/873,548, filed on Jun. 21, 2004, which is also incorporated by reference in its entirety and for all purposes. It should be noted that the present invention is not limited to the embodiments disclosed in the aforementioned U.S. patent application Ser. No. 10/873,548. Rather, any network of sensors and actuators can be employed, regardless of whether they are incorporated into a flexible substrate or not. The invention simply contemplates sensors and actuators that are attached to structures in any manner that allows for analysis according to the methods described herein. One of skill will realize that many different approaches exist for attaching sensors and actuators to a structure, not all of which employ flexible substrates. Accordingly, the diagnostic layers illustrated herein are used for purposes of convenience only, and sensor networks that do not employ layers can be employed as well.

Figure 1B:
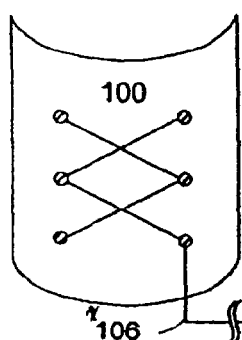
FIGS. 1B-1C illustrate block and circuit diagrams, respectively, describing elements of a sensing layer and their operation.
Figure 1B:
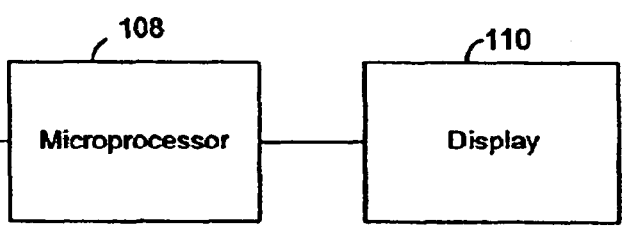

FIG. 1B further describes aspects of the operation of the diagnostic layer 100. In operation, the output leads 106 are electrically connected to an analysis unit such as a microprocessor 108, suitable for analyzing signals from the sensors 102. In certain embodiments, the flexible layer 100 is first attached to a structure in a manner that allows the sensing elements 102 to detect quantities related to the health of the structure. For instance, the sensors 102 can be sensors configured to detect stress waves propagated within the structure, and emit electrical signals accordingly. The microprocessor 108 then analyzes these electrical signals to assess various aspects of the health of the structure. For instance, detected stress waves can be analyzed to detect crack propagation within the structure, delamination within composite structures, or the likelihood of fatigue-related failure. Quantities such as these can then be displayed to the user via display 110.

Figure 1C:
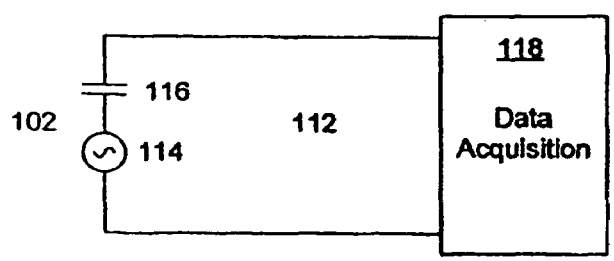

In one embodiment, the sensors 102 can be piezoelectric transducers capable of reacting to a propagating stress wave by generating a voltage signal. Analysis of these signals highlights properties of the stress wave, such as its magnitude, propagation speed, frequency components, and the like. Such properties are known to be useful in structural health monitoring. FIG. 1C illustrates a circuit diagram representation of such an embodiment. This embodiment can often be represented as a circuit 112, where each sensor 102 is represented as a voltage source 114 in series with a capacitor 116 (impedance circuitry) used to adjust signal strength. This pair is in electrical contact with a data acquisition unit 118, such as a known data acquisition card employed by microprocessors 108 (the data acquisition unit 118 can be thought of as a component interface to the microprocessor 108). Propagating stress waves induce the sensor 102 to emit a voltage signal that is recorded by the data acquisition unit 118, where it can be analyzed to determine the health of the structure in question. As discussed below, these piezoelectric transducers can also act as actuators, converting an applied voltage to a stress wave signal. In another embodiment, the sensors 102 can be known fiber optic sensors that convert stress waves to optical signals.

Figure 2A:
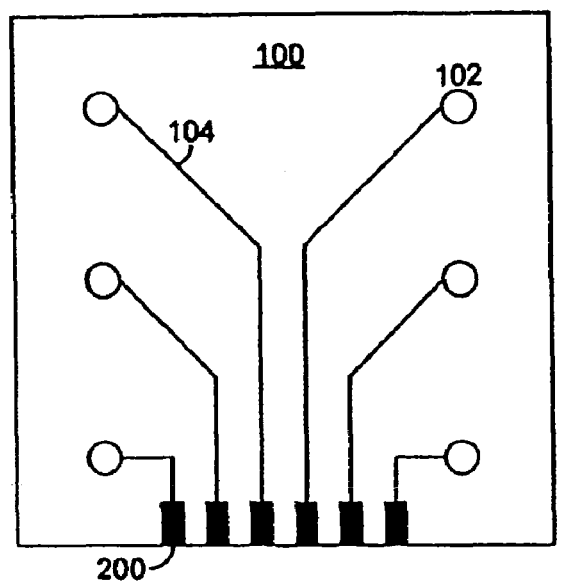
FIG. 2A illustrates a top view highlighting further details of a sensing layer having a two-dimensional array of sensors.
Figure 2B:
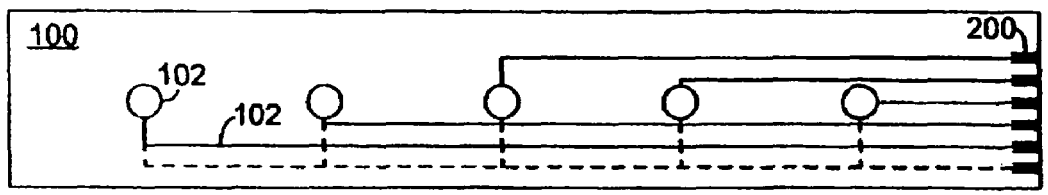
FIG. 2B illustrates a top view highlighting further details of a sensing layer having a one-dimensional array of sensors.

FIG. 2A illustrates further details of a sensing layer 100. It should be noted that the invention includes sensing layers 100 configured in any number of ways. For instance, the sensors 102 can be distributed in any manner throughout the layer 100. Here, six such sensors 102 are shown regularly distributed in a two-dimensional array, each with a single trace 104 extending to the contacts 200. However, one of skill will observe that the sensors 102, traces 104, and contacts 200 can be distributed in any manner, and in any number, without departing from the scope of the invention. For example, the sensors 102 can also be configured in a one-dimensional array such as that shown in FIG. 2B. Here, instead of two rows of sensors 102, a single row is employed. Such a one-dimensional array finds uses in, for example, the monitoring of areas too narrow to fit a two-dimensional array.

Figure 3:
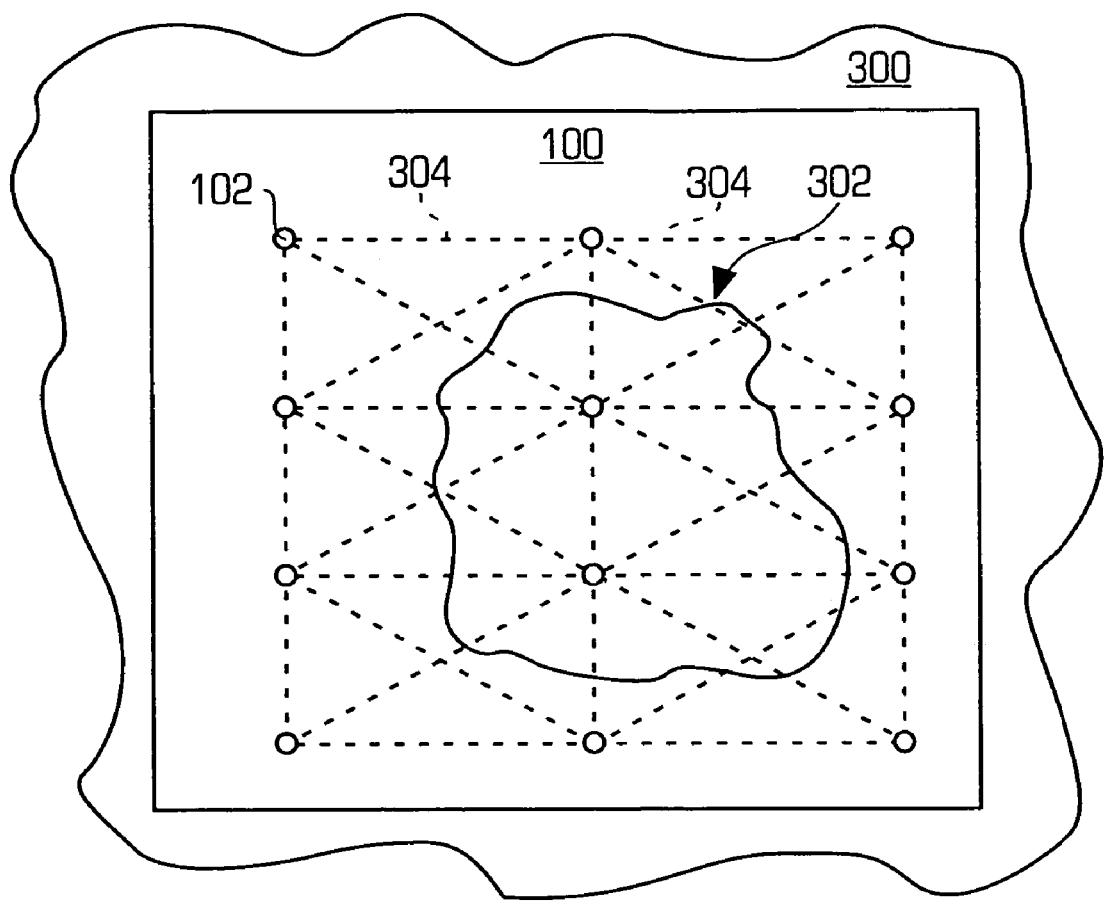
FIG. 3 illustrates a sensing layer and sensors/actuators configured to analyze a damage region of a structure in accordance with embodiments of the present invention.

FIG. 3 illustrates a diagnostic layer 100 and sensors/actuators configured to analyze a damage region of a structure in accordance with embodiments of the present invention. The diagnostic layer 100 is attached to a structure 300, allowing it to detect and analyze damage regions 302 via transducers 102 that can be either passive sensors or actuators.

The location and size of the damage region are determined according to at least three methods. In the first "through path" method, stress waves are sent along paths directly between pairs of sensors/actuators. If this path intersects a portion of the damage region, the stress waves are altered. The manner in which these stress waves are altered is then used to determine the size and location of the damage region. While this method analyzes those stress waves that travel directly through the damage region, the second method, or "reflection" approach, instead analyzes those stress waves that are reflected from the damage region. The properties of these reflected stress waves are then analyzed according to triangulation or other methods, so as to determine the size and location of the damage region. The third, or "phased array" method, involves synchronizing multiple stress waves from different actuators, so as to generate a focused stress wave that propagates along a particular path. If this path intersects the damage region, a reflected stress wave will be detected. Multiple focused stress waves are directed along different paths of the structure. In this manner, a series of beams is "swept" across the structure, and the location and size of the damage region is determined according to any corresponding reflected stress waves.

In the through path approach, stress waves are sent out by various ones of the sensors/actuators 102. Those stress waves sent along paths 304 that do not intersect the damage region 302 will remain unchanged, while those stress waves sent along paths 304 that do intersect the damage region 302 will be altered. Such altered signals indicate which paths 304 intersect the damage region 302, in turn offering an indication of the location of the damage region 302 as well as a rough indication of its size (the greater the number of paths 304 that intersect the damage region 302, the larger the damage region 302 is). Also, passing through the damage region 302 typically alters the stress waves in such a manner that their energy is reduced. This reduction in energy can then be analyzed to determine the approximate severity of the damage done, which together with the number of paths 304 gives a more complete assessment of the "size" of the damage region, both in terms of the amount of area on the structure 300 that is affected, as well as how badly that area is affected. Thus, for instance, the methods of the invention can determine the location of a damage region 302 on a structure 300, the physical size of the damage region 302, and how badly that region is damaged. The methods of the invention can thus pinpoint a damage region 302 and determine its size, as measured both by its physical dimensions and how badly the structure 300 has been affected. The invention can thus distinguish between damage regions 302 that are large but relatively mild (e.g., a large but shallow dent), and small but severe damage regions 302 that may actually be of more concern (e.g., a small hole in the structure, or a short but deep crack).

In the reflection approach, paths 304 are not directly analyzed. Instead, actuators 102 emit stress waves, some of which reflect off the damage region 302. These reflected stress waves are then analyzed to determine the size and location of the damage region 302. While the invention contemplates various analysis methods, one embodiment employs triangulation. In this approach, three different actuators/sensors 102 are employed. Each transmits a stress wave whose reflection is detected by the other two. The times of flight (i.e., the times between transmission of stress waves, and reception of their reflections) of each of these reflected waves, along with the positions of each of the three actuators/sensors 102, are used along with the wave velocity to triangulate the location of the damage region 302. Similar to the through path approach, the energy reduction in the reflected waves is also calculated and can be used to determine the size and severity of the damage region 302.

In the phased array approach, multiple actuators 102 emit stress waves with predetermined phase differences so as to focus a composite beam upon a predetermined point, thereby forming a stress wave beam along a specified direction. Some embodiments can employ known ray acoustics methods to generate such a beam. In other embodiments, actuators 102 can employ known digital beamforming or other methods to generate such directional beams. In essence, directional stress waves are sent out from the actuators 102, with reflections indicating whether, and how far away, a damage region 302 was encountered. The structure can effectively be swept with multiple directional stress waves, to get a complete picture of the size, shape, and location of the damage region 302.

Because certain embodiments allow for devices that can function as both sensors and actuators, it should be noted here that the methods of the invention can be practiced with devices that are used in this dual role. That is, while sensing is described as being performed by groups of sensors and stress wave generation is described as being performed by groups of actuators, it is possible for any device to be used as a sensor during detection of a load change, and as both a sensor and an actuator during the subsequent location/size analysis. Also, it is to be understood that, in many embodiments, the terms "sensor" and "actuator" can be used to describe any device shown on layer 100, and references to groups of sensors or groups of actuators can include any such device, even if the groups include common devices.

Figure 4:
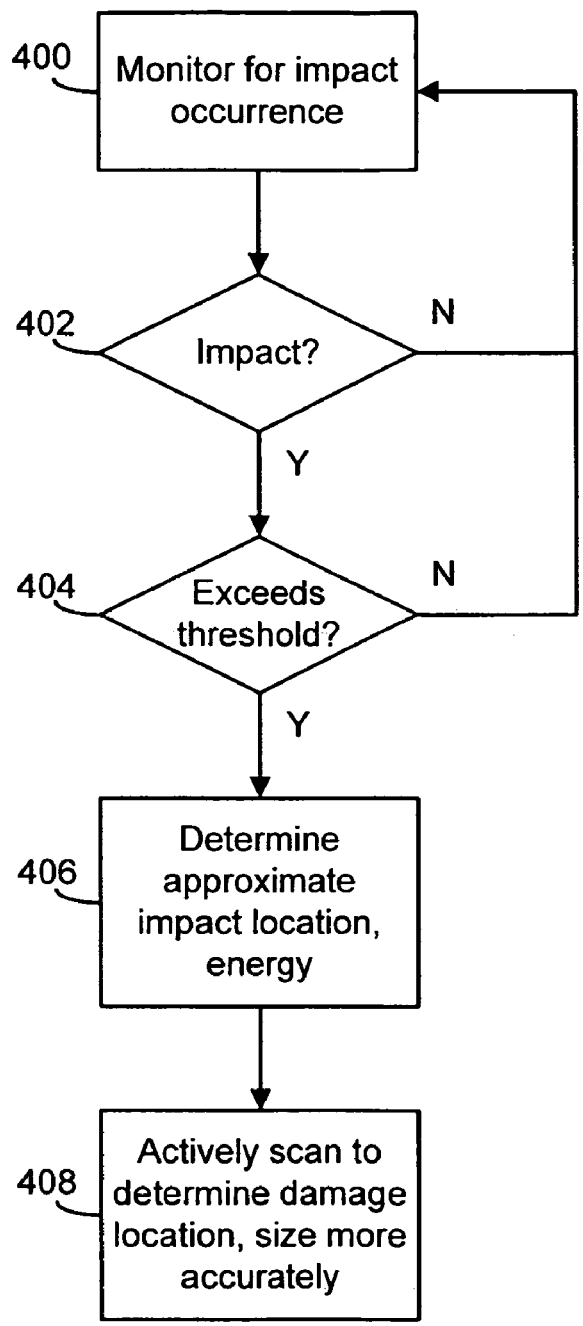
FIG. 4 illustrates process steps in the detection and analysis of a damage region.

FIG. 4 illustrates process steps in the detection and analysis of a damage region 302. Once the layer 100 is installed on the structure 300, it can monitor the structure for the presence of an impact (step 400). To conserve energy, this step can be performed with passive sensors 102, rather than actively via the actuators 102. More specifically, the sensors 102 simply generate a voltage upon exposure to the stress waves generated by an impact upon the structure. When an impact or other load change of concern is accordingly detected (step 402), the processor 108 determines whether the load change exceeds some threshold indicating a load change that requires further analysis (step 404). The exact threshold, or thresholds, used are not central to the invention, and any may be used. For instance, the threshold may be a critical value of stress wave magnitude or energy, a combination of both, or a duration over which the stress wave energy exceeds a certain amount.

Once the threshold is exceeded, the responses from all passive sensors 102 are employed to determine the load change's approximate location and energy (step 406). The methods and apparatuses involved in carrying out this step are further described in co-pending U.S. patent application Ser. No. 10/928,788, which is hereby incorporated by reference in its entirety and for all purposes.

While it is useful to determine information regarding the load change that caused the damage, it is often more useful to determine the extent of the damage caused by that load change. To that end, the actuators 102 also emit stress waves to determine the location and size of the damage region more accurately (step 408). As above, such a determination can be made by a through path analysis, a reflection analysis, or a phased array approach. Accordingly, attention now turns to illustration of these three methods.

Through Path Analysis

Figure 5A:
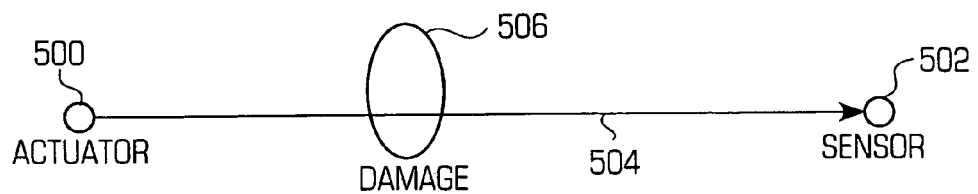
FIGS. 5A-5C illustrate concepts underlying through-path analysis of a damage region.

FIG. 5A conceptually illustrates one context in which through path analysis is employed. In through path analysis, stress waves are transmitted from one actuator 500, along a through path 504, directly to a sensor 502. If the stress waves pass through a damage region 506, the properties of the waves are altered. Any change in these properties can be analyzed to determine the size of the damage. Similarly, the number of through paths 504 that pass through the damage region 506 illustrates both the size and location of the damage region 506.

Figure 5B:
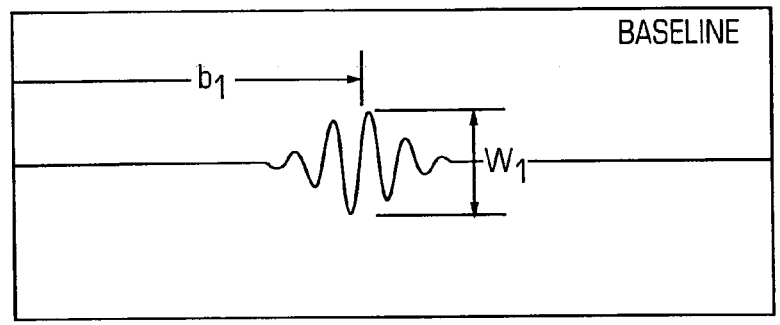
Figure 5C:
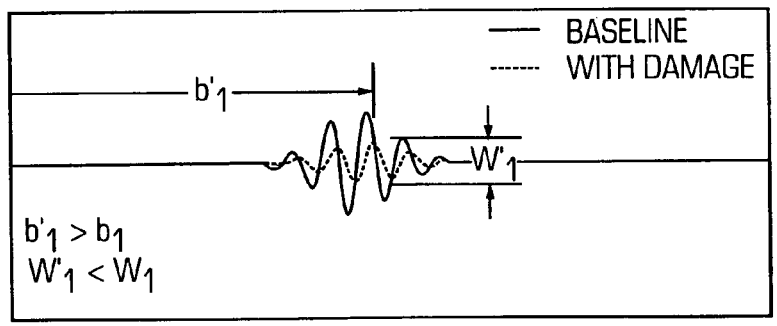

FIGS. 5B-5C graphically illustrate property changes that stress waves undergo when transmitted through a damage region 506. More specifically, FIG. 5B illustrates an exemplary stress wave signal as generated by an actuator 500, before passing through the damage region 506. If the damage region 506 were absent, this signal would reach the sensor 502 at time $b_1$, and having an amplitude $w_1$. FIG. 5C illustrates this same stress wave signal both before and after passing through the damage region 506. In passing through the damage region 506, the stress wave is slowed and its amplitude is reduced. Accordingly, stress waves passing through the damage region 506 will be detected at sensor 502 with a reduced amplitude $w_1'$, and an increased arrival time $b_1'$. Thus, one way to determine whether a stress wave has passed through the damage region 506 is to determine whether its amplitude has been reduced, and its arrival time increased, relative to the original stress wave signal sent by actuator 500. Such an analysis can indicate the number of through paths 504 that intersect the damage region 506, thus indicating its location and giving one indicator of its size/severity. The reduction in amplitude also can be used to determine the amount of energy the stress wave lost in traveling through the damage region 506, also giving an indicator of the size/severity of the damage region 506.

Figure 6:
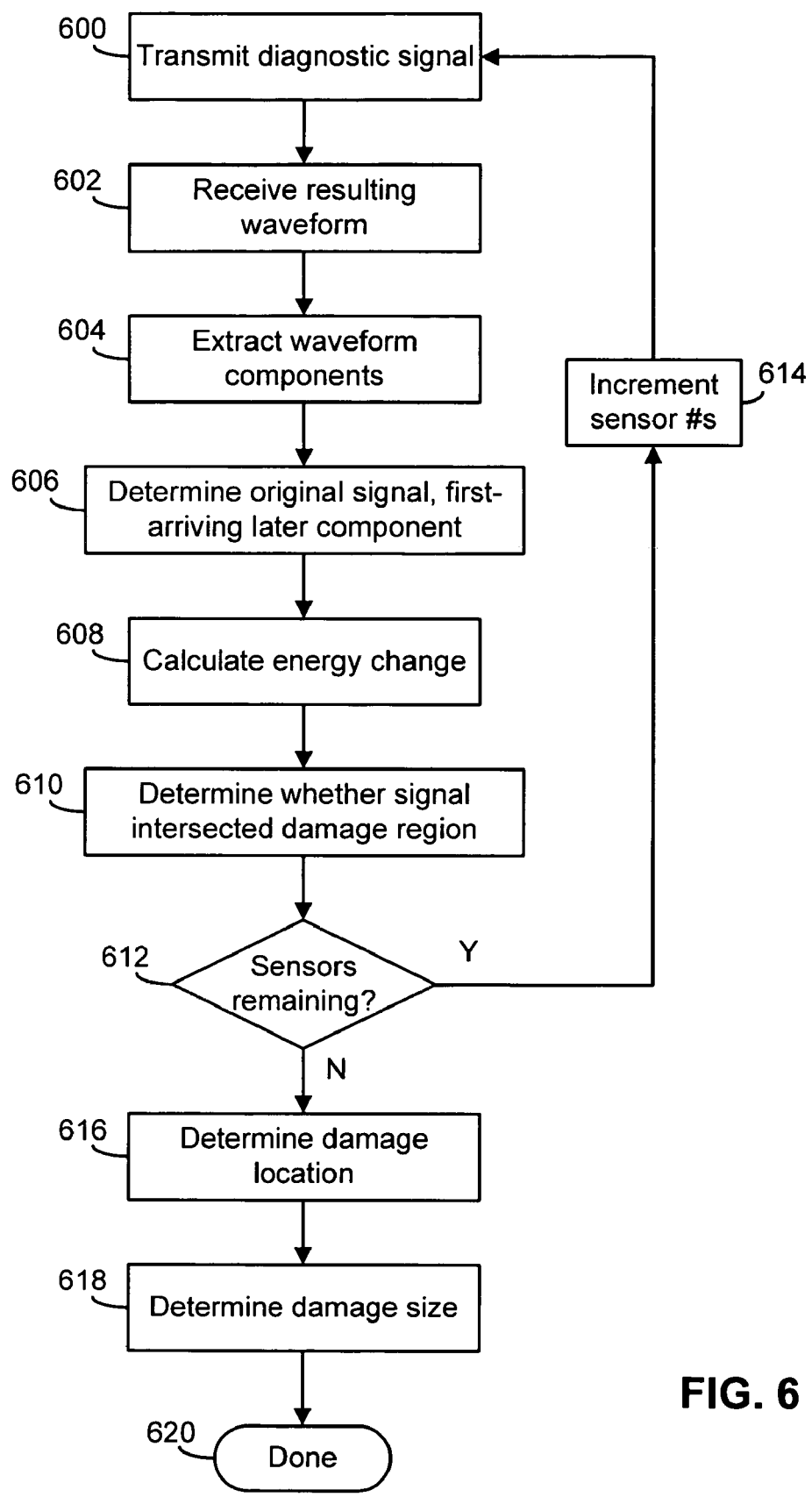
FIG. 6 illustrates process steps in the through-path analysis of a damage region.

Essential concepts of the through path method having been explained, FIG. 6 illustrates process steps in the through-path analysis of a damage region. An actuator 500 first transmits a stress wave signal, such as that shown in FIG. 5B, to a sensor 502 via a through path 504 (step 600). The stress wave signal passes through the damage region 506, is altered (i.e., amplitude reduced and arrival time increased), and the resulting waveform is received by the sensor 502 (step 602). As the exact geometry of the damage region 506 can be complex, and multiple stress wave reflections can also be generated, the waveform received at the sensor 502 contains many different components. As only certain components are useful in a through path analysis (components representing reflections, for instance, are useful in a reflection analysis, but not in a through path analysis, as these components are reflected off the damage region 506, and do not pass directly through it), the individual waveform components must be extracted for analysis (step 604). The first component to be detected by the sensor 502 is deemed to have traveled through the damage region 506, if any, due to the fact that it has traveled the shortest path, i.e., directly from the actuator 500 to the sensor 502 (step 606). Accordingly, its energy is calculated (step 608) and the component is analyzed to determine whether it has passed through the damage region 506 (step 610). This process is repeated with different actuators 500 and sensors 502 so as to analyze different through paths 504 (steps 612-614).

In some embodiments of the invention, the determination of whether a stress wave component has passed through the damage region 506 is made according to that component's strain energy, defined as:

$$\int_0^t |s(t)|^2 \, dt$$

where s(t) is the time-dependent stress wave component of interest. In this case, s(t) is the first-detected component of the waveform received by the sensor 502.

Once the strain energy of a component is calculated, it can be compared to the strain energy of the stress wave before it passed through the damage region 506. As this original stress wave is known, its strain energy can be calculated beforehand and stored for retrieval by the processor 108. If the difference between the strain energy of the originally-transmitted stress wave and the strain energy of the first-detected component is greater than a threshold amount, the stress wave, and thus its through path 504, are deemed to have passed through the damage region 506. If the difference is less than this amount, the through path 504 is deemed not to intersect the damage region 506.

Once a sufficient number of through paths 504 have been analyzed, the location of the damage region 506 is determined (step 616). In one embodiment, the location is determined according to the locations of the through paths deemed to intersect the damage region 506. More specifically, the location of the damage region 506 can be determined as the geometric centroid (i.e., the geometric center of the midpoints of each through path 504 that intersects the damage region 506) of all the through paths 504 that are deemed to intersect the damage region 506. The invention also contemplates determination of the location of the damage region 506 according to other methods, and is not limited to calculation of the centroid. As one example, some embodiments of the invention may simply employ the locations of the through paths that intersect the damage region 506 to sketch an outline of the size, shape, and location of the damage region 506.

Other embodiments of the invention employ different methods of determining the location of the damage region 506. For example, one alternate embodiment examines the total strain energy detected by a given transducer 102, rather than the strain energy of a single component. More specifically, the strain energy of the $k^{th}$ passive sensor is given by:

$$E_k = \int_{t_i}^{t_f} |s_k(t)|^2 \, dt$$

where $t_i$ is the initial time of the time window associated with the time of trigger and $t_f$ is the final time of the time window. Using an averaging approach such as the following weighted average approach to find the impact location:

$$\bar{x} = \frac{\sum_{k=1}^{N} x_k \int_{t_i}^{t_{f1}} |s_k(t)|^2 \, dt}{\sum_{k=1}^{N} \int_{t_i}^{t_{f1}} |s_k(t)|^2 \, dt}$$

$$\bar{y} = \frac{\sum_{k=1}^{N} y_k \int_{t_i}^{t_{f1}} |s_k(t)|^2 \, dt}{\sum_{k=1}^{N} \int_{t_i}^{t_{f1}} |s_k(t)|^2 \, dt}$$

where x-bar and y-bar represent the approximate location of the damage region 506. Accordingly, the location of the damage region 506 can be determined by an analysis of either specific components of an impact's stress waves, or the total stress waves themselves. The invention contemplates use of both approaches.

Analysis of the extracted wave components also allows for a determination of the size of the damage region 506 (step 618). As above, the term "size" in certain embodiments includes both the surface area of the damage region 506, as well as an indication of the severity of the damage within that region 506. The invention contemplates calculation of the size of the damage region 506 according to any method that yields a workable estimation of the physical size and/or severity of the damage to the structure 300. Many different calculation methods exist. For example, one embodiment calculates the geometric size of the damage region 506 as the surface area outlined by the midpoints of each through path 504 that is found to intersect the damage region 506.

In one embodiment, an estimation of the severity of the damage done can also be determined by examining the energy changes of each wave component that passes through the damage region 506. The greater the energy change of the wave components, the more energy is dissipated by the damage region 506, which implies more severe damage. The energy change need not be correlated to a specific type of damage. For example, certain applications may not be concerned with the length of a particular crack, but may only be concerned with whether the crack is propagating or not. In cases such as these, the energy change over time may be the only quantity of interest. Other embodiments may, however, require a correlation between energy change and a specific type of damage. The relation between energy changes and more specific forms of damage (i.e., energy changes of a certain nature, or above a certain threshold, imply a hole in the structure) is a function of the specific geometry and material of the structure 300. A different relationship must thus be developed for each structure to be monitored. The invention contemplates the development of such relationships by any known method, including both empirical and theoretical methods.

In another embodiment, an estimation of the severity of the damage done can be based at least partly on the detected maximum force of an impact. The determination of the maximum force relies on the use of the sensor energy based on a unique time window size, which may or may not be the same as that used for calculating the impact location. This corresponds to a new value, $t_{f2}$. The formula that represents this approach is given below:

$$E_T = \sum_{k=1}^{N} \int_{t}^{t_{f2}} |s_k(t)|^2 \, dt$$

$$F_{max} = f(E_T)$$

The maximum force $F_{max}$ can be correlated to specific types of damage by employing theoretical or empirical models, as above.

Once an appropriate relationship is created, the processor 108 correlates the energy changes to a degree or type of damage according to this relationship, and the resulting information is output to the display 110. The location and size of the damage region 506 having been determined, the process terminates (step 620).

Figure 7A:
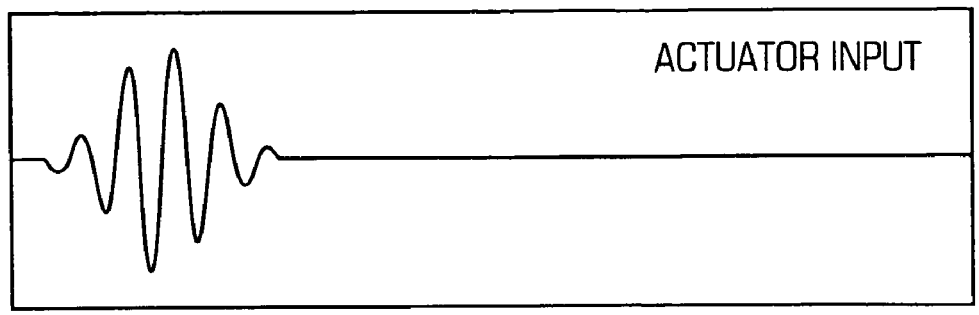
FIG. 7A illustrates stress waves for transmission through a structure during through-path analysis of a damage region.

It should be noted that the exact form of the stress waves sent and received, and the exact methods of their analysis, are simply specific embodiments of the invention. The invention is not limited to specific forms of waves sent/received, nor is it limited by the methods used in their analysis. Rather, it includes simply the passive sensing of load changes, and subsequent active interrogation to determine information such as damage location and size. However, in the interest of clarity, a specific example is given to more fully illustrate the concepts of the invention. The process steps of FIG. 6 are accomplished by transmitting known stress wave profiles and analyzing those that have propagated through the damage region 506. FIG. 7A illustrates one such wave profile that has been found to work in some structures. In this embodiment, actuator 500 transmits a five cycle windowed sine burst signal, as shown. In this specific example, a Hanning window is used to concentrate energy at the desired driving frequency, although any suitable window can be used. In plate-like structures, these stress waves propagate through the structure 300 according to Lamb wave analysis. Namely, the waves behave according to the Rayleigh-Lamb dispersion equation, where a finite number of symmetric and anti-symmetric modes (roots) travel independently:

$$\frac{\tan(\bar{d}\sqrt{1-\alpha^2})}{\tan(\bar{d}\sqrt{\beta^2-\alpha^2})} + \left[\frac{4\alpha^2\sqrt{1-\alpha^2}\sqrt{\beta^2-\alpha^2}}{(2\alpha^2-1)^2}\right]^{\pm 1} = 0$$

where +1 is used for symmetric roots, and −1 is used for anti-symmetric roots, and where $$\alpha^2 = \frac{c_t^2}{c_{ph}^2}, \beta^2 = \frac{c_t^2}{c_l^2}, \bar{d} = \frac{k_t h}{2}$$

$$c_t^2 = \frac{\mu}{\rho}, c_l^2 = \frac{(\lambda + 2\mu)}{\rho}, k_t = \frac{\omega}{c_t}$$

$$\mu = \frac{E}{2(1+v)}, \lambda = \frac{Ev}{(1-2v)(1+v)}$$

For a given material with known values of Young's Modulus (E), Poisson's Ratio (v), and density (ρ), the phase velocity ($c_{ph}$) and the frequency-thickness product (ωh) must be numerically solved. Once the phase velocity dispersion curve is obtained, the group velocity dispersion curve can be obtained from:

$$f = 2\pi\omega, \quad k = \frac{2\pi}{\text{wavelength}}, \quad c_{ph} = \frac{\omega}{k}$$

$$v_g = \frac{\partial \omega}{\partial k}$$

where $v_g$ represents the group velocity, $\omega$ the angular frequency, and k the real wave number.

Figure 7B:
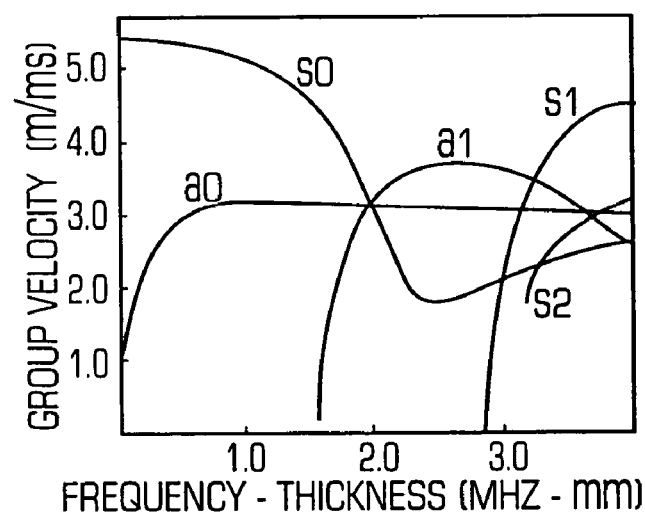
FIG. 7B illustrates group velocity dispersion curves for use in through-path analysis of a damage region.

The number of group velocity dispersion curves is a known function of the frequency-thickness product. The Rayleigh-Lamb equation is solved for the various group dispersion curves, resulting in a graph similar to FIG. 7B, which illustrates the group velocity dispersion curves of different modes propagating through a known aluminum alloy. It should be noted that the group velocity dispersion curves partly depend on the properties of the medium, and also vary with propagation direction in anisotropic media.

Figure 8A:
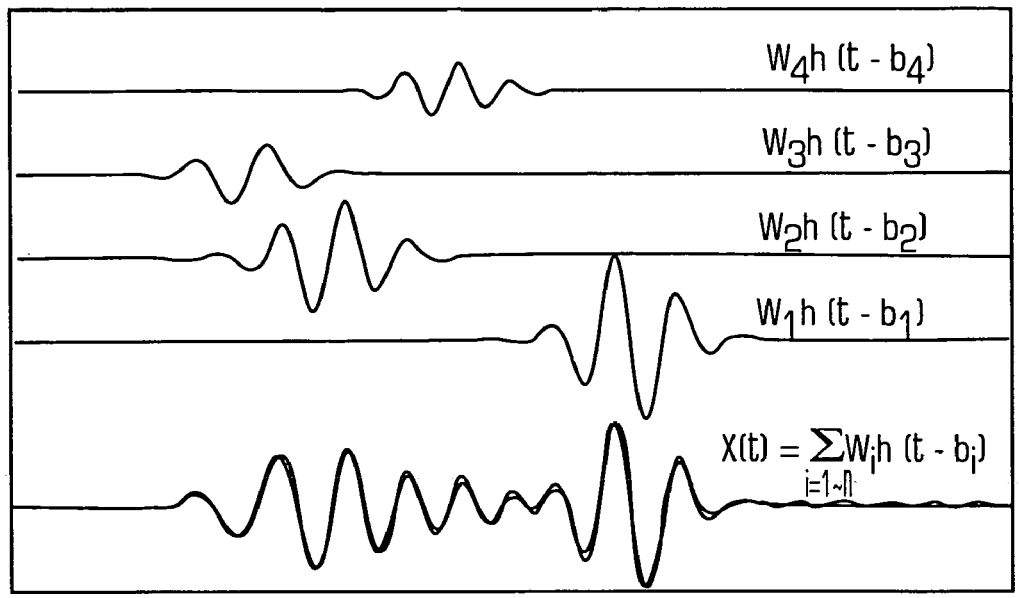
FIG. 8A graphically illustrates waveform decomposition for through-path analysis of a damage region.
Figure 8B:
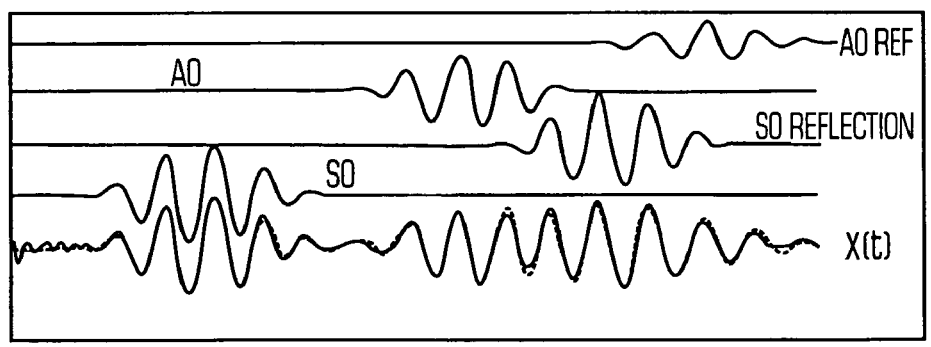
FIG. 8B graphically illustrates the correlation of decomposed waveform components to waveform groups.

Once an actuator transmits the stress wave signal shown in FIG. 7A, the wave propagates through the structure 300, where it passes through and/or reflects off of the damage region 506. The sensors thus receive a waveform that looks similar to that shown at the bottom of FIG. 8A, i.e. a signal that contains the originally-transmitted stress wave (in modified form if it passed through the damage region 506), superposed on top of any number of reflections. This complex signal is then decomposed into its various components, for individual analysis. Decomposition is accomplished in this embodiment by assuming that the measured waveform is constructed of a series of superposed wave components of the form:

$$x(t) = \sum_{i=1}^{M} w_i h_i(t) + e(t)$$

where $w_i$ is the amplitude of the wave component, $e(t)$ is the perturbation (error), and $h_i(t)$ is the shape of the wave component shown in FIG. 7A:

$$h_i(t) = \exp\left(-\left(\frac{t-b_i}{\sigma_i}\right)^2\right)\sin(\omega_i(t-b_i))$$

where $\sigma_i$ and $\omega_i$ are given constants and b is the arrival time. Assuming this form of the detected waveform allows the waveform to be broken down, in known fashion, into its various wave components, as shown in FIG. 8A. Here, the wave is composed of four different components.

Each wave component and its features are then extracted successively, using methods such as known cross-correlation methods, in which a best match for each wave component is found, subtracted from the received waveform signal, and the process is repeated until no more components are found. The two main features that are extracted from each wave component are the arrival time, $b_i$, and the amplitude, $w_i$:

$$r_0(t) = x(t)$$

$$r_i(t) = r_{i-1}(t) - w_i h_i(t)$$

-continued $$b_i = \left\{b \mid |\langle r_i(t), h(t-b)\rangle| = \max_b |\langle r_i(t), h(t-b)\rangle|\right\}$$

$$w_i = \frac{|<r_i(t), h(t-b_i)>|}{|<h(t-b_i), h(t-b_i)>|}$$

Once the waveform is decomposed into its various components and the arrival time and amplitude of each are determined, the process proceeds according to which method is being employed. If the through path method is employed, the first-arriving components (the component with the shortest arrival time) of each transmitted stress wave are analyzed. Their strain energies are calculated as above, and a determination is made as to whether the stress wave intersected the damage region 506. This can be accomplished by comparing the strain energy to a threshold value to determine whether the reduction in energy exceeded a certain amount, or it can be accomplished by comparing the arrival time to the arrival time the stress wave would have if the damage region 506 did not exist. The latter value is simply the distance between the actuator and sensor, divided by the velocity of the stress wave in the medium of the structure 300, and in the direction between the actuator and sensor. As all these quantities are known, this value can be calculated ahead of time and stored for retrieval by the processor 108.

In the through path method, the process is repeated for each through path 504, and the damage location is determined according to the centroid of each through path 504 that is determined to intersect the damage region 506. Alternately, as described earlier, the total strain energy of each sensor can be examined and a weighted average or similar approach can be employed. Similarly, the damage size is determined according to the area outlined by each through path that intersects the damage region 506, as well as by the amount of strain energy dissipated for each stress wave transmitted, or by the maximum detected impact force.

Figure 9:
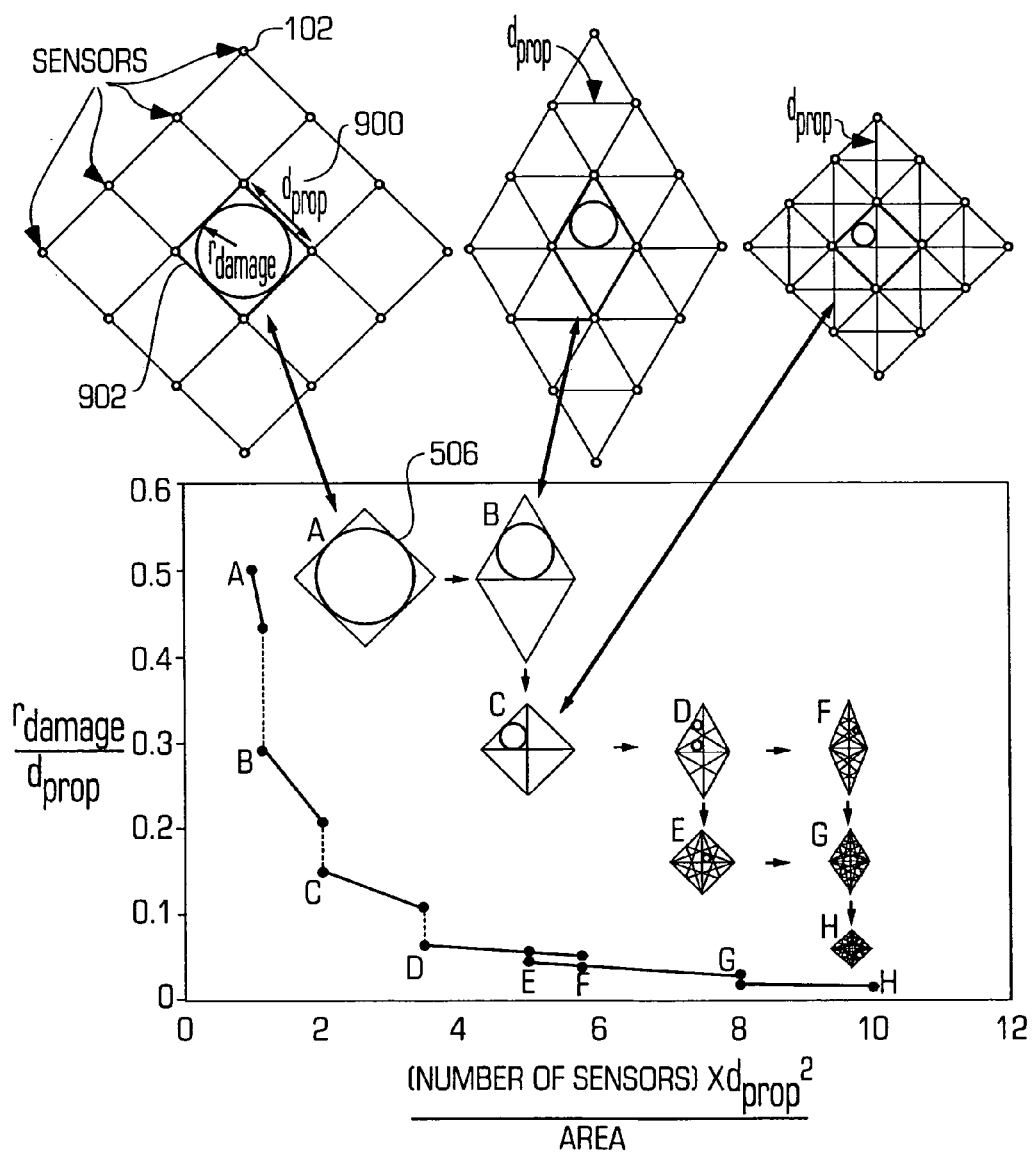
FIG. 9 illustrates one approach to sensor/actuator density and placement in accordance with embodiments of the present invention.

In the through path method, one of skill will observe that the minimum detectable damage size depends on the number and length of through paths 504. Accordingly, the sensitivity of the layer 100 depends on the number and arrangement of actuators/sensors 102. As illustrated in FIG. 9, the density of actuators/sensors 102 on the layer 100 is a predictable function of the size of the damage region 506 (assuming a specific geometry, e.g., a circular damage region 506 in this case) and the propagation distance 900 that a stress wave can travel before becoming undetectable or otherwise unusable by the methods herein. As seen in FIG. 9, the minimum detectable damage size is a decreasing function of the sensor density. Hence, the ability to detect small damage regions 506 requires dense networks of sensors/actuators 102. Also, while sparse sensor networks may be desirable in certain contexts (such as to reduce the cost of the layer 100), the sensors/actuators 102 must still be arranged with a certain minimum density according to the propagation distance 900, or else accurate analysis of the damage region 506 cannot occur. Accordingly, the invention includes the placement of sensors/actuators 102 according to the minimum damage size that is desired to be detected, and the propagation distance 900 of the sensors/actuators 102. Within these parameters, the invention contemplates many arrangements of actuators/sensors 102, such as those shown in A-H of FIG. 9.

Reflection Analysis

Figure 10A:
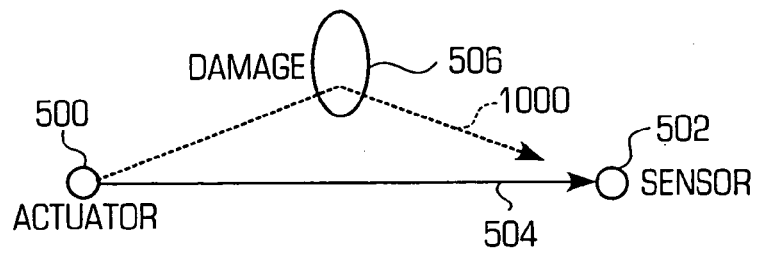
FIGS. 10A-10C illustrate concepts underlying reflection analysis of a damage region.

FIG. 10A conceptually illustrates one context in which reflection analysis is employed. In reflection analysis, stress waves are transmitted from an actuator 500 to a sensor 502 as in through path analysis. However, instead of analyzing those stress waves that travel directly from the actuator 500 to the sensor 502, this method instead analyzes those stress waves that are reflected from damage regions 506 that do not lie along the through path 504. When these stress waves 1000 are reflected, their properties are altered by their interaction with the damage region 506.

Figure 10B:
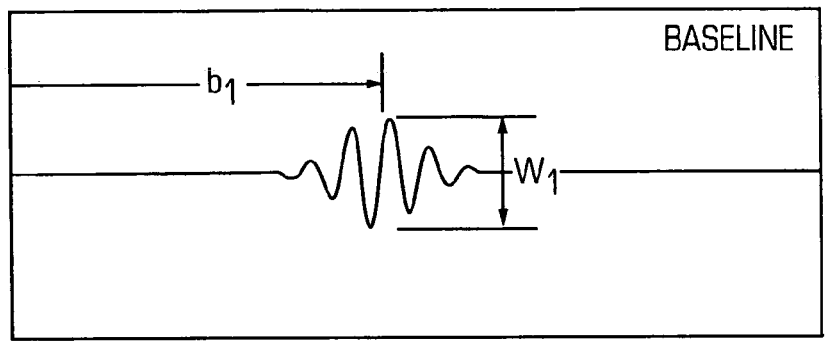
Figure 10C:
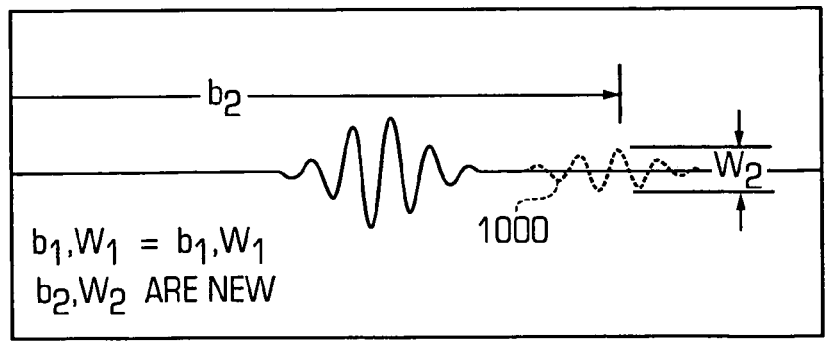

FIGS. 10B-10C graphically illustrate property changes that stress waves undergo when reflected from a damage region 506. A stress wave 1000 is generated by the actuator 500, as shown in FIG. 10B. This stress wave 1000 travels the through path 504, arriving at the sensor 502 time $b_1$ and having an amplitude $w_1$. However, the stress wave 1000 also travels off the through path 504, reflecting off the damage region 506 as shown. In reflecting, the properties of the stress wave 1000 are altered. Also, as the path taken is less direct than that of the through path 504, the reflected stress wave 1000 arrives at the sensor 502 later than the component that traveled directly along the through path 504.

More specifically, FIG. 10B illustrates an exemplary stress wave signal as generated by an actuator 500, before passing through the damage region 506. If the damage region 506 were absent, this signal would reach the sensor 502 at time $b_1$, and having an amplitude $w_1$. FIG. 10C illustrates this same stress wave signal as detected at the sensor 502, along with the time-delayed component reflected from the damage region 506. The reflected stress wave signal 1002, reflected from the damage region 506, will be detected at sensor 502 with an amplitude $w_2$, and an arrival time $b_2$ that has been delayed significantly compared to the arrival times of waves delayed in through path analysis. The amount of delay, as well as the amplitude, indicate both the location and size/severity of the damage region 506.

Figure 11:
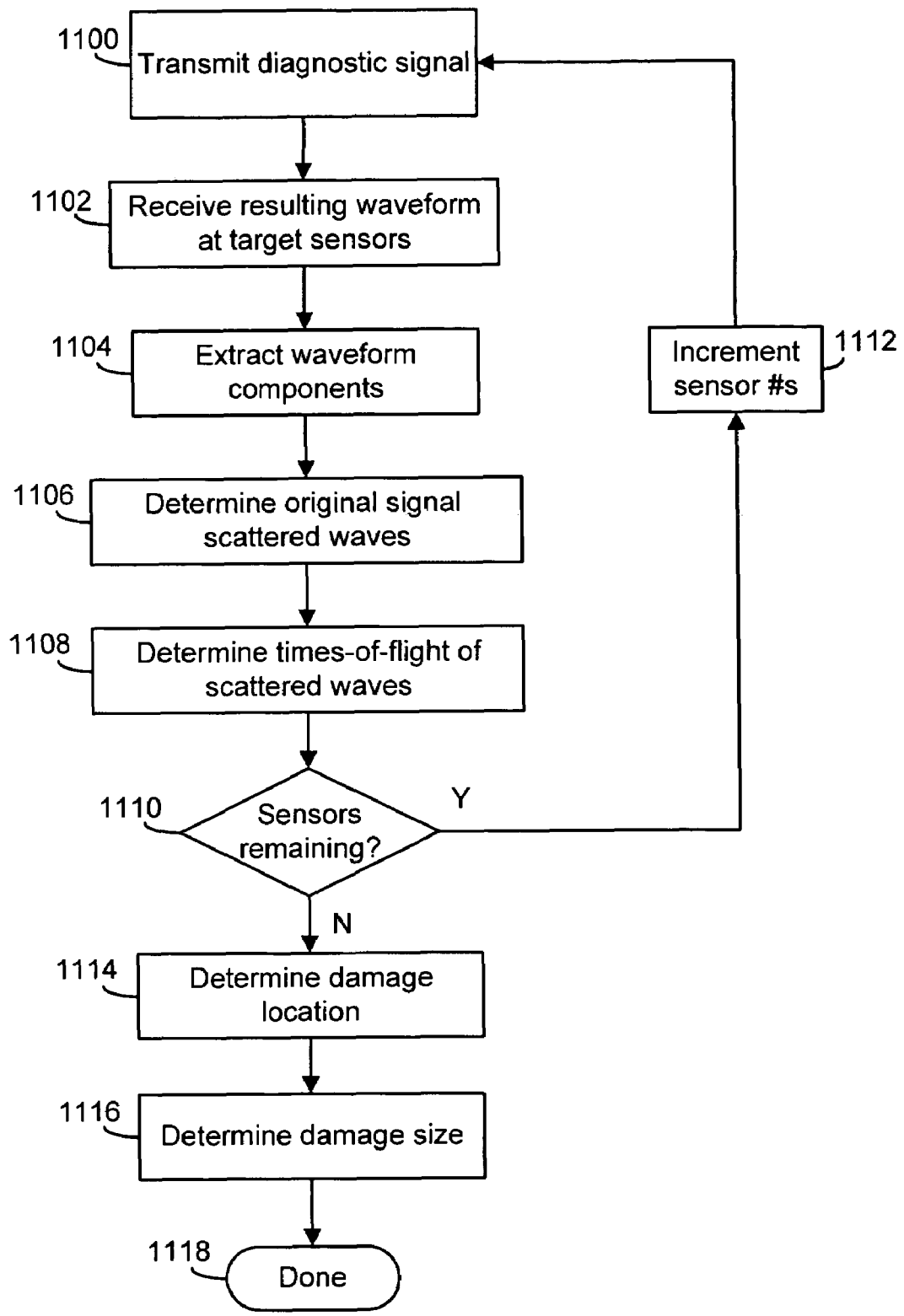
FIG. 11 illustrates process steps in the reflection analysis of a damage region.

Essential concepts of the reflection analysis method having been explained, FIG. 11 illustrates process steps in the reflection analysis of a damage region 506. An actuator 500 first transmits a stress wave signal, such as that shown in FIG. 10B (step 1100). This stress wave signal propagates in all directions along the structure 300, including toward the damage region 506 and directly along the through path 504. Components of the stress wave will thus be received from the actuator 500, and reflected from the damage region 506. These components are received at the target sensors 502 (step 1102). The various components of the received waveform are then extracted in the same manner as explained above with regard to through path analysis (step 1104). Inspection of the extracted components reveals which are the original stress wave and which are the reflected waves scattered from the damage region 506 (step 1106). The times-of-flight, or times from transmission to detection by the sensor 502, are then determined (step 1108) and the process is repeated for further actuators/sensors (steps 1110-1112). The received signals and their times of flight are then analyzed to determine the location (step 1114) and size (step 1116) of any damage, whereupon the process ends (step 1118).

Steps 1100-1104 are, in some embodiments, substantially identical to the corresponding steps taken in through path analysis. That is, stress wave transmission, reception, and component extraction can be performed in the same fashion as that described above. After that, the reflection analysis differs. Unlike through path analysis, reflection analysis does not focus on the first-received component, but rather focuses on later-received components. These components are the ones deemed to have reflected off the damage region 506, as their longer flight times imply reflection from the damage region 506 rather than travel along the through path 504. Accordingly, these later-received components, or components scattered by the damage region 506, are the focus of reflection analysis.

As with the discussion of through path analysis above, reflection analysis as employed by the invention is not limited to the embodiments shown. However, in the interest of clarity, a specific example is given to more fully illustrate the concepts of the invention. The process steps of FIG. 11 are accomplished in this example by a triangulation process employing three sensors/actuators 102 at a time. Two sensors 102 each transmit stress waves to each other and to a third sensor 102. Reflections from the pair of transmitted stress waves are analyzed by the three sensors. Analysis of the properties of these reflections, along with knowledge of the positions of each of the three sensors, allows for a determination of damage region 506 location and size information.

Figure 12A:
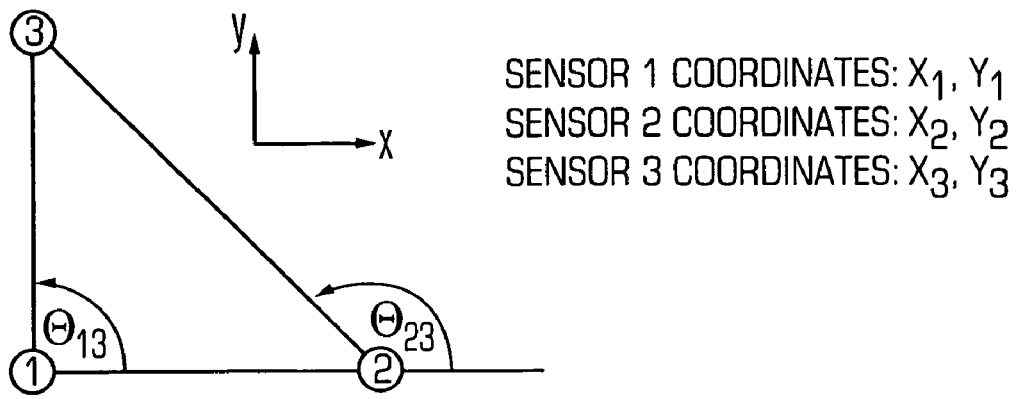
FIGS. 12A-12C illustrate concepts underlying reflection analysis of a damage region according to triangulation methods.
Figure 12B:
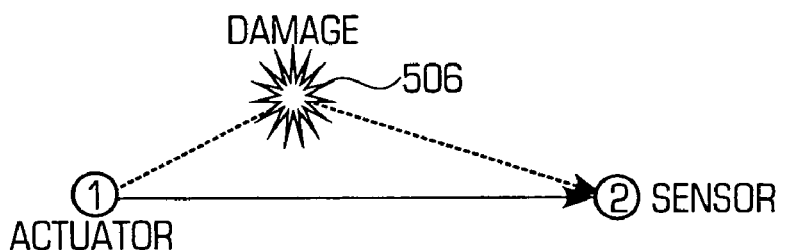
Figure 12C:
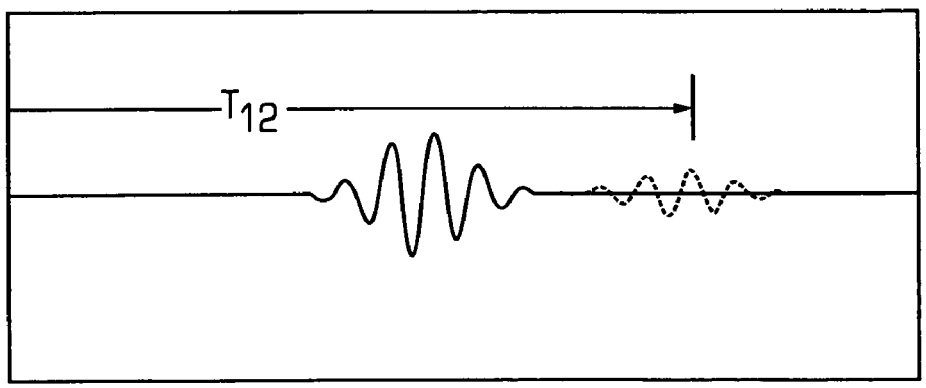

FIGS. 12A-12C illustrate an exemplary sensor layout and a triangulation analysis employing this layout. FIG. 12A illustrates three sensors 1-3 and three actuator-sensor paths (1→2, 1→3, and 2→3). When damage is present, the propagating stress wave will be scattered or reflected off of the damage, as illustrated in FIG. 12B. For known values of the sensor coordinates ($X_1$, $Y_1$, $X_2$, $Y_2$, $X_3$, $Y_3$), the path angles ($\theta_{13}$, $\theta_{23}$), detected times-of-flight ($T_{12}$, $T_{13}$, $T_{23}$), and the wave velocity (v), three ellipses can be mathematically constructed, each having two of the sensors 1-3 as their foci and all three intersecting at a point (x, y) that is the location of the damage:

$$\frac{\left(x\cos\theta_{13} + y\sin\theta_{13} - \frac{X_1 + X_3}{2}\right)^2}{\left(\frac{vT_{13}}{2}\right)^2} + \frac{\left(-x\sin\theta_{13} + y\cos\theta_{13} - \frac{Y_1 + Y_3}{2}\right)^2}{\left(\frac{vT_{13}}{2}\right)^2 - (X_1 - X_3)^2 - (Y_1 - Y_3)^2} = 1$$

$$\frac{\left(x\cos\theta_{23} + y\sin\theta_{23} - \frac{X_2 + X_3}{2}\right)^2}{\left(\frac{vT_{23}}{2}\right)^2} + \frac{\left(-x\sin\theta_{13} + y\cos\theta_{13} - \frac{Y_2 + Y_3}{2}\right)^2}{\left(\frac{vT_{23}}{2}\right)^2 - (X_2 - X_3)^2 - (Y_2 - Y_3)^2} = 1$$

$$\frac{\left(x\cos\theta_{23} + y\sin\theta_{23} - \frac{X_2 + X_3}{2}\right)^2}{\left(\frac{vT_{23}}{2}\right)^2} + \frac{\left(-x\sin\theta_{13} + y\cos\theta_{13} - \frac{Y_2 + Y_3}{2}\right)^2}{\left(\frac{vT_{23}}{2}\right)^2 - (X_2 - X_3)^2 - (Y_2 - Y_3)^2} = 1$$

These three equations are then solved simultaneously to find the coordinates (x, y) of the intersection point (location of damage). Thus, this triangulation approach employs successive sets of three sensors 102, two of which transmit a stress wave signal and all three of which detect the reflections therefrom. Once the reflections detected at each sensor 1-2 are isolated and times-of-flight determined, as in FIG. 12C, sufficient information exists to simultaneously solve the three equations above to determine the location of the damage region 506.

Once the location of the damage region 506 is determined, the process can be repeated with a different set of three sensors 102. Step 1114 then involves calculating an "overall" location from the various locations coordinates (x, y) determined for each set of three sensors. The invention includes any such method of calculation, including determining the location as the geometric centroid of every (x, y) location determined.

The location of the damage region 506 having been determined, the size/severity is also calculated. As with through path analysis, the surface area of the damage region 506 can be determined according to the area outlined by each calculated location (x, y). Measures of severity can also be calculated according to the amount of strain energy dissipated for each stress wave transmitted. As above, the invention contemplates a determination of severity according to any method, from simple comparison to a threshold amount of strain energy dissipated, to correlation with a theoretical or empirical model of damage to the specific structure 300 being monitored.

It should be noted here that the reflection analysis simply analyzes reflected stress waves such as those shown in FIG. 12C. The invention therefore includes any known method for calculating the location of a region according to stress waves reflected from it, of which the above-mentioned triangulation approach is but one.

Phased Array Analysis

Figure 13:
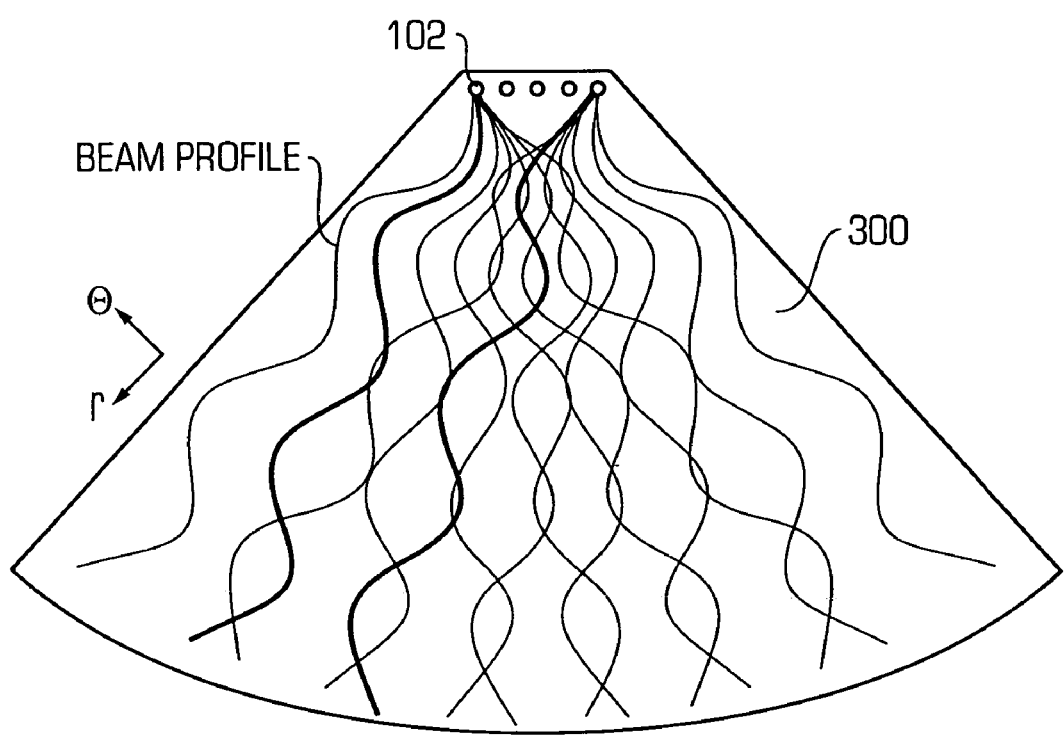
FIG. 13 illustrates concepts underlying phased array analysis of a damage region.

FIG. 13 conceptually illustrates an implementation of phased array analysis. In phased array analysis, stress waves from actuators 102 are transmitted through the structure 300 in specific phase relations to each other, so as to generate a directional stress wave "beam" that is focused along a particular direction within the structure 300. This directional stress wave is focused along various directions of the structure, with reflections indicating intersection with the damage region 506. Times-of-flight of the reflected stress waves also indicate the distance of that portion of the damage region 506 intersected, assuming the wave propagation velocity (v) is known. In this manner, a directional stress wave can be successively focused along different directions, or "swept" across the structure 300 to determine the location and size of the damage region 506.

The directional stress wave beam is generated by simultaneously transmitting stress waves from multiple actuators 102, some of which are delayed relative to others.

The delay (positive or negative) can be determined using ray acoustics techniques, essentially focusing multiple stress waves upon a single, predetermined point in the structure. The path length from the actuator to this "field point" gives the propagation time and this is adjusted relative to some reference point. The propagation time $t_i$ from the actuator to the field point is:

$$t_i = \frac{1}{c}\sqrt{(x_i - x_f)^2 + (y_i - y_f)^2 + (z_i - z_f)^2}$$

where $(X_f, y_f, Z_f)$ is the position of the focal point, $(x_i, y_i, z_i)$ is the position of actuator number i, and c is the wave speed along the appropriate direction of the structure 300.

A point is selected on the array as a reference for the imaging process. The propagation time for this is:

$$t_c = \frac{1}{c}\sqrt{(x_c - x_f)^2 + (y_c - y_f)^2 + (z_c - z_f)^2}$$

where $(x_c, Y_c, z_c)$ is the reference center point on the array. The time by which to delay stress waves from each actuator of the array is then:

$$\Delta t_i = \frac{1}{c}\Big(\sqrt{(x_c - x_f)^2 + (y_c - y_f)^2 + (z_c - z_f)^2} - \sqrt{(x_i - x_f)^2 + (y_i - y_f)^2 + (z_i - z_f)^2}\Big)$$

Notice that there is no limit on the selection of the different points, and thus the beam can be steered in a preferred direction.

As can be seen above, an added advantage of phased array analysis lies in the ability to focus the stress wave beam at a single point within the structure (i.e., focusing along both the radial and tangential directions simultaneously), so as to derive a much more accurate picture of the damage region 506. In this manner, once the location of the damage region 506 is roughly known, such as by a first pass of the beam across the damage region 506, the beam can be focused on different points in that area so as to scan the local area of the damage region 506 much more thoroughly.

Figure 14:
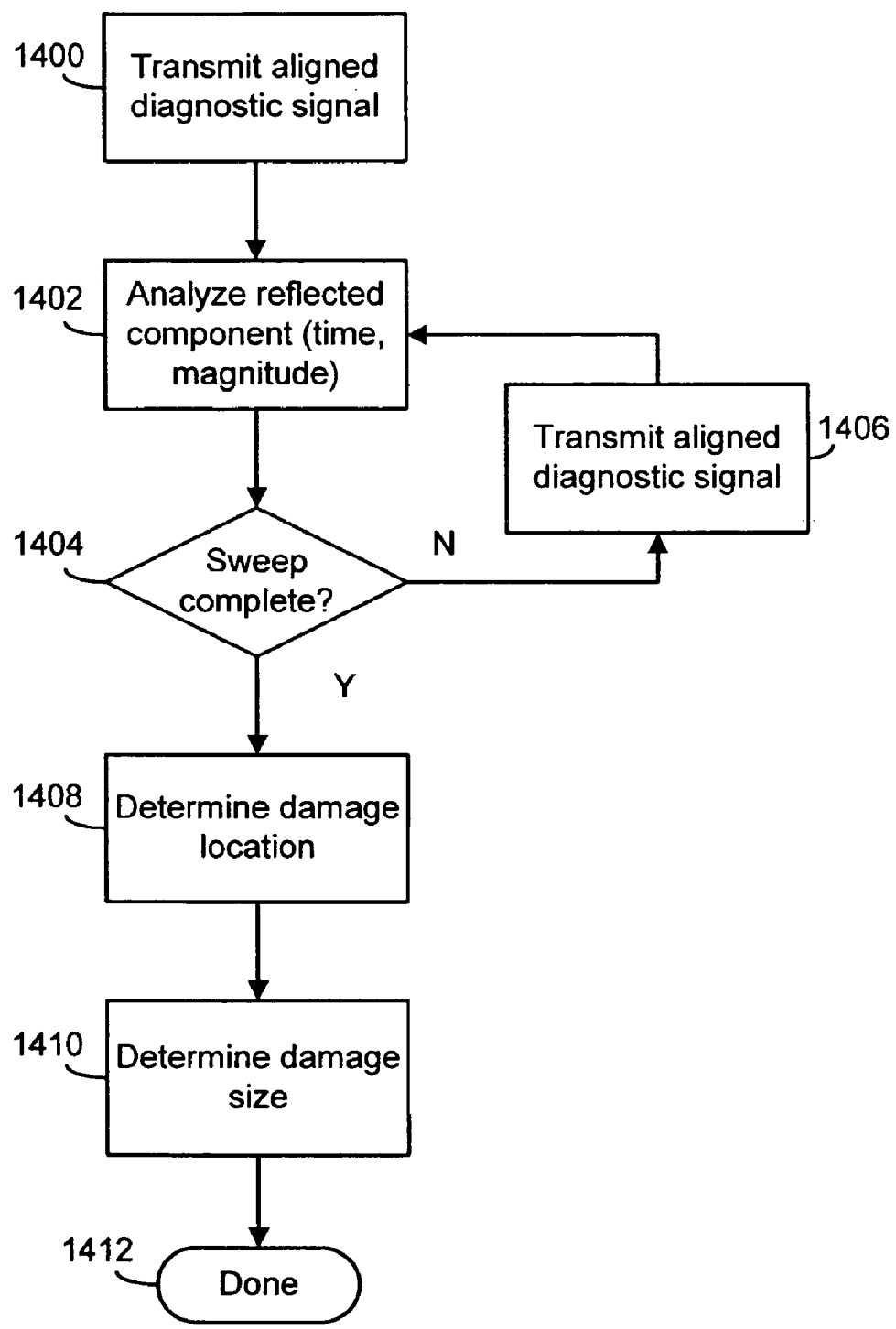
FIG. 14 illustrates process steps in the phased array analysis of a damage region.

In this method, as in through path analysis, the first-received reflections are analyzed and their times-of-flight employed to determine the location of the damage region 506. Also as above, the reduction in amplitude can be used to calculate the size of the damage region 506. FIG. 14 illustrates process steps involved on one embodiment employing phased array analysis. A focused stress wave is first sent from actuators 102 along a particular direction of the structure 300 (step 1400). The actuators 102 each transmit stress waves, some of which are time delayed according to the above expressions, that interact so as to generate such an aligned beam. The first-received reflected component is isolated as above, and analyzed to determine its flight time and magnitude reduction, if any (step 1402). This step can be accomplished with the component isolation and analysis methods previously described. This process is repeated with beams focused along different directions of the structure, so as to sweep focused stress beams across the entire structure (steps 1404-1406). The beamforming process can be accomplished by either transmitting re-aligned diagnostic signals, or by varying the delay (positive or negative) of previously recorded signals from the transducers 102. The first-received components, or reflected signals, if any, are then analyzed as above to determine the location (step 1408) and size (step 1410) of the damage region 506, whereupon the process terminates (step 1412).

The essential functions of the sensor network having been described, attention now turns to an alternate embodiment of the invention. Here, as above, a sensor layer 1500 includes a number of sensors 1502 and actuators 1504 (again, recall that a single set of transducers can act as both sensors 1502 and actuators 1504), each connected to switches 1506, which are connected to a microprocessor 1508. As above, the microprocessor 1508, in a "passive mode," interprets signals from the sensors 1502 to determine the occurrence of an impact, then directs the switches 1506 to switch to an "active mode" by switching to actuators 1504. This electrically connects the actuators 1504 to transmit stress waves so as to determine the location and severity of the impact's damage location. The results can then be shown on the display 1510. The switches 1506 can be known two position switches that toggle between a first position connecting the sensors 1502 to the microprocessor 1508, and a second position connecting the actuators 1504 to the microprocessor 1508.

Upon detecting such an impact, switches 1506 can toggle to disconnect the sensors 1502 and connect the actuators 1504 to the microprocessor 1508, allowing the microprocessor 1508 to direct the actuators 1504 to transmit stress waves and analyze the characteristics of the impact's damage region. Such a configuration allows for automatic toggling between sensors 1502 and actuators 1504, eliminating the need to manually disconnect and reconnect wires when switching the microprocessor 1508 between sensors 1502 and actuators 1504.

Figure 15A:
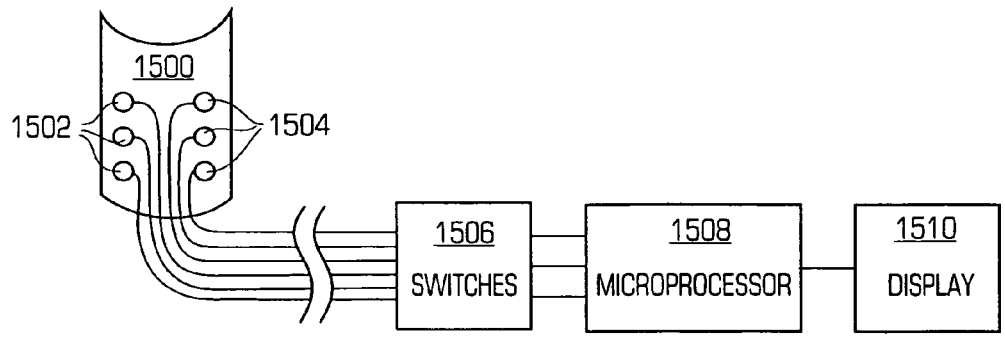
FIG. 15A illustrates a block diagram of an alternate embodiment of the invention, incorporating switches for toggling between sensors and actuators.
Figure 15B:
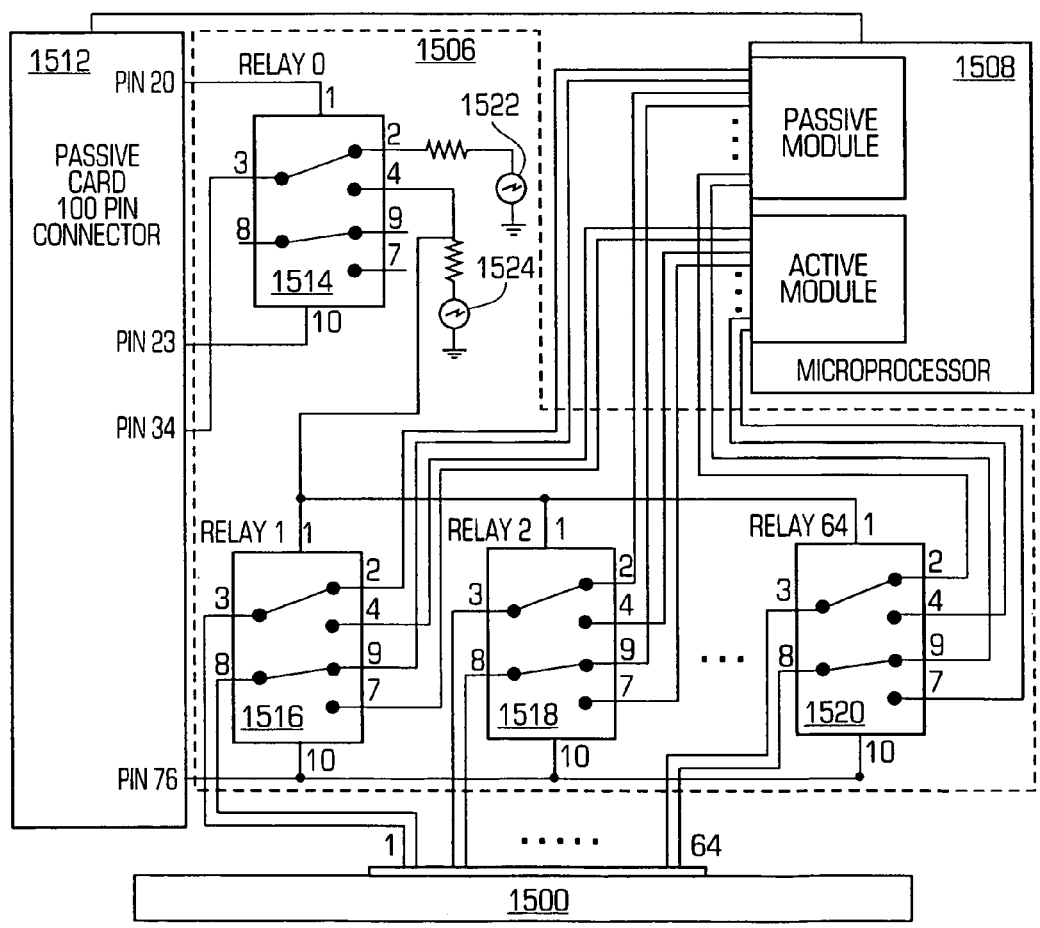
FIG. 15B illustrates a circuit diagram of the switches of FIG. 15A.

FIG. 15B is a circuit diagram illustrating further details of the switches 1506. As shown, relays 1516-1520 are in first positions connecting electrical lines 3 and 8 to lines 2 and 9 respectively, thus electrically connecting the sensors 1502 to the microprocessor 1508. If the microprocessor 1508 is configured with a separate passive module containing circuitry for detecting and analyzing signals from the sensors 1502, this configuration allows connection between the sensors 1502 and the passive module. So connected, the microprocessor 1508 is able to receive signals from the sensors 1502.

Upon detecting an impact, the microprocessor 1508 must switch to the actuators 1504 to query the structure as detailed above. Accordingly, the microprocessor 1508 sends a signal to pin 20 of the interface 1512, directing the relay 1514 to switch to its second position, connecting its lines 3 and 8 to lines 4 and 7, respectively. This in turn toggles the relays 1516-1520 to their lines 4 and 7, as well as switching off the first indicator light 1522 (indicating passive mode is no longer on), and switching on the second indicator light 1524 (indicating active mode is now on). The switching of relays 1516-1520 to their lines 4 and 7 disconnects the microprocessor 1508 from the sensors 1502 and connects it with the actuators 1504, whereupon the active querying of the structure, as described above, can begin. One of skill will realize that the use of such switches 1506 is preferable to manually disconnecting and/or reconnecting the sensors 1502 and actuators 1504 when switching between active and passive modes.

Note that the invention encompasses the use of separate hardware for controlling the active and passive modes as shown. The invention also encompasses the integration of active mode controllers and passive mode controllers into a single microprocessor 1508, as such controller integration is known.

The foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description. They are not intended to be exhaustive or to limit the invention to the precise forms disclosed. Many modifications and variations are possible in view of the above teachings. For example, while embodiments of the invention employ five cycle Hanning-windowed sine burst signals, the invention contemplates the use of any stress wave signal suitable for detection and analysis of damage in a structure. Also, while methods such as through path and reflection analysis are explained, the invention contemplates the use of any method in the active analysis of structures to determine damage location and size. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A structural health monitoring system, comprising:
a plurality of passive sensors coupled to a structure;
a plurality of actuators coupled to the structure; and
a controller in electrical communication with the plurality of passive sensors and the plurality of actuators, the controller configured to receive from the plurality of passive sensors an indication of a load change generating a damage region on a structure, the damage region having a location and a size, the controller further configured to direct the plurality of actuators to transmit stress waves through the structure in response to the indication of a load change, so as to determine the location and the size of the damage region.

2. The structural health monitoring system of claim 1 wherein the actuators are spatially distributed along the structure so as to facilitate the determination of the location and the size of the damage region by directing the stress waves through the damage region, for receiving by either others of the active sensors or by the passive sensors.

3. The structural health monitoring system of claim 2 wherein the actuators are configured to transmit the stress waves to a maximum distance through the structure so as to facilitate the detection of a minimum size of the damage region within a monitored surface area of the structure, and wherein the actuators are placed in a spatial distribution, the spatial distribution generally determined according to the maximum distance, the minimum size of the damage region, the number of the actuators, and the monitored surface area of the structure.

4. The structural health monitoring system of claim 2 wherein the controller is further configured to direct successive ones of the actuators to transmit the stress waves through the damage region, to isolate first-detected components of the transmitted stress waves detected prior to later-detected components of the transmitted stress waves, and to analyze the first-detected components so as to determine the location and the size of the damage region.

5. The structural health monitoring system of claim 4 wherein the controller is further configured to determine whether ones of the first-detected components have passed through the damage region, and to determine the location of the damage region according to the first-detected components that have passed through the damage region.

6. The structural health monitoring system of claim 4 wherein the controller is further configured to determine energy changes of ones of the first-detected components that have passed through the damage region, and to determine the size of the damage region at least partially according to the energy changes.

7. The structural health monitoring system of claim 1 wherein the actuators are spatially distributed along the structure so as to facilitate the determination of the location and the size of the damage region by directing the stress waves upon the structure, and by detecting reflected stress waves generated by reflections of the stress waves from the damage region.

8. The structural health monitoring system of claim 7 wherein the controller is further configured to direct successive threes of the actuators to transmit the stress waves through the structure, to detect the corresponding reflected stress waves at the threes of the actuators and at ones of either the passive sensors or the actuators, and to analyze the detected stress waves so as to facilitate a determination of the location and the size of the damage region.

9. The structural health monitoring system of claim 8 wherein the controller is further configured to determine departure times at which the stress waves are transmitted, to determine arrival times at which the corresponding reflected stress waves are detected, to determine wave travel times approximately equal to the difference between the departure times and the corresponding arrival times, and to determine the location of the damage region at least partially according to the wave travel times and to positions at which the corresponding reflected stress waves are detected.

10. The structural health monitoring system of claim 8 wherein the controller is further configured to determine energy changes of the reflected stress waves, and to compare the energy changes to an energy change profile so as to determine the size of the damage region.

11. The structural health monitoring system of claim 1 wherein the actuators are spatially distributed along the structure so as to facilitate the determination of the location and the size of the damage region by focusings of the stress waves along the structure.

12. The structural health monitoring system of claim 1 wherein both the passive sensors and the actuators are piezoelectric transducers configured to generate and to receive the stress waves.

13. The structural health monitoring system of claim 1 wherein both the passive sensors and the actuators are fiber optic transducers configured to generate and to receive the stress waves.

14. The structural health monitoring system of claim 1 wherein the plurality of passive sensors and the plurality of actuators are affixed to a flexible substrate, and wherein the flexible substrate is attached to the structure.

15. A method of analyzing a damage region of a structure, comprising:
receiving a first set of stress waves generated by a load change upon a structure, the load change also generating a damage region on a structure, the damage region having a location and a size; and
in response to the receiving, transmitting a second set of stress waves though the structure so as to facilitate a determination of the location and the size of the damage region.

16. The method of claim 15 wherein the transmitting further includes sequentially transmitting ones of the second set of stress waves though a plurality of paths along the structure, the method further comprising analyzing portions of the transmitted stress waves that are transmitted along the paths, so as to determine the location and the size of the damage region.

17. The method of claim 16 wherein the analyzing further includes isolating first-detected wave components of each of the portions of the transmitted stress waves that are transmitted along the paths, and determining energy changes of the first-detected wave components that have passed through the damage region.

18. The method of claim 17 further comprising determining, according to the energy changes, those paths that intersect the damage region, and determining the location of the damage region according to the positions along the structure of those paths that intersect the damage region.

19. The method of claim 17 further comprising determining the size of the damage region according to at least the energy changes and the ones of the paths that intersect the damage region.

20. The method of claim 15 wherein the transmitting further includes transmitting successive pairs of the stress waves through the structure, detecting corresponding reflected stress waves that are reflected from the damage region, and analyzing the reflected stress waves so as to determine the location and the size of the damage region.

21. The method of claim 20 wherein the analyzing further includes isolating first-detected wave components of each of the reflected stress waves, and isolating later-detected wave components of each of the reflected stress waves, the later-detected wave components received after the first-detected wave components.

22. The method of claim 21 wherein the analyzing further includes determining departure times at which the pairs of the stress waves are transmitted, determining arrival times at which the corresponding reflected stress waves are detected, subtracting the departure times from the corresponding arrival times to determine travel times of the reflected stress waves, and calculating the location of the damage region at least partially according to the travel times and the positions along the structure at which the reflected stress waves are detected.

23. The method of claim 22 wherein the calculating further includes calculating the location of the damage region according to a triangulation of the travel times and the positions along the structure.

24. The method of claim 21 wherein the analyzing further includes determining energy changes of the first-detected wave components reflected from the damage region.

25. The method of claim 24 wherein the analyzing further includes comparing the energy changes to an energy change profile so as to determine the size of the damage region.

26. The method of claim 15 wherein the analyzing further includes successively focusing ones of the second set of stress waves along the structure and detecting corresponding reflected stress waves reflected from the damage region, so as to determine the location and the size of the damage region.

27. A computer readable memory storing instructions to direct a computer to function in a specified manner, comprising:
first instructions to receive a first set of stress waves generated by a load change upon a structure, the load change also generating a damage region on a structure, the damage region having a location and a size; and
second instructions to transmit, in response to the receiving, a second set of stress waves through the structure so as to facilitate a determination of the location and the size of the damage region.

28. The computer readable memory of claim 27 wherein the second instructions further comprise instructions to sequentially transmit ones of the second set of stress waves through a plurality of paths along the structure, the computer readable memory further comprising third instructions to analyze the portions of the transmitted stress waves that are transmitted along the paths, so as to determine the location and the size of the damage region.

29. The computer readable memory of claim 28 wherein the third instructions further comprise instructions to isolate first-detected wave components of each of the portions of the transmitted stress waves that are transmitted along the paths, the computer readable memory further comprising a fourth instructions to determine energy changes of the first-detected wave components that have passed through the damage region.

30. The computer readable memory of claim 29 further comprising fifth instructions to determine, according to the energy changes, those paths that intersect the damage region, and sixth instructions to determine the location of the damage region according to the positions along the structure of those paths that intersect the damage region.

31. The computer readable memory of claim 29 further comprising fifth instructions to determine the size of the damage region according to at least the energy changes and the ones of the paths that intersect the damage region.

32. The computer readable memory of claim 27 wherein the second instructions further comprise instructions to transmit successive pairs of the stress waves through the structure, the computer readable memory further comprising third instructions to detect corresponding reflected stress waves that are reflected from the damage region, and fourth instructions to analyze the reflected stress waves so as to determine the location and the size of the damage region.

33. The computer readable memory of claim 32 wherein the fourth instructions further comprise instructions to isolate first-detected wave components of each of the reflected stress waves, and to isolate later-detected wave components of each of the reflected stress waves, the later-detected wave components received after the first-detected wave components.

34. The computer readable memory of claim 33 further comprising fifth instructions to determine departure times at which the pairs of the stress waves are transmitted, to determine arrival times at which the corresponding reflected stress waves are detected, to subtract the departure times from the corresponding arrival times to determine travel times of the reflected stress waves, and to calculate the location of the damage region at least partially according to the travel times and the positions along the structure at which the reflected stress waves are detected.

35. The computer readable memory of claim 34 wherein the fifth instructions further comprise instructions to calculate the location of the damage region according to a triangulation of the travel times and the positions along the structure.

36. The computer readable memory of claim 33 wherein the fourth instructions further comprise instructions to determine energy changes of the first-detected wave components reflected from the damage region.

37. The computer readable memory of claim 36 wherein the fourth instructions further comprise instructions to compare the energy changes to an energy change profile so as to determine the size of the damage region.

38. The computer readable memory of claim 27 wherein the second instructions further comprise instructions to successively focus ones of the second set of stress waves along the structure and detecting corresponding reflected stress waves reflected from the damage region, so as to determine the location and the size of the damage region.

39. A structural health monitoring system, comprising:
 a plurality of passive sensors configured to facilitate the analysis of a structure;
 a plurality of actuators configured to facilitate the analysis of the structure;
 switches having first configurations establishing electrical connections with the plurality of passive sensors and second configurations establishing electrical connections with the plurality of actuators; and
a controller in electrical communication with the switches, the controller configured to toggle the switches to the first configurations so as to receive from the plurality of passive sensors an indication of a load change generating a damage region on a structure, and to the second configurations so as to direct the plurality of actuators to transmit stress waves through the structure in response to the indication of a load change, to facilitate a determination of the location and the size of the damage region.

40. The structural health monitoring system of claim 39 wherein the controller is further configured to toggle the switches to the first configurations so as to establish electrical connections between the controller and the plurality of passive sensors, and to the second configurations so as to establish electrical connections between the controller and the plurality of actuators.

41. The structural health monitoring system of claim 40 wherein the controller is further configured to determine a location of the damage region on the structure, and to selectively direct those of the actuators proximate to the location to transmit the stress waves through the structure.

* * * * *

UNITED STATES PATENT AND TRADEMARK OFFICE
CERTIFICATE OF CORRECTION

PATENT NO. : 7,458,266 B2 Page 1 of 1
APPLICATION NO. : 11/060650
DATED : December 2, 2008
INVENTOR(S) : Shawn J. Beard et al.

It is certified that error appears in the above-identified patent and that said Letters Patent is hereby corrected as shown below:

On the title page item (73), The Assignee should be:
ACELLENT TECHNOLOGIES, INC.

Signed and Sealed this

Twenty-ninth Day of September, 2009

David J. Kappos
*Director of the United States Patent and Trademark Office*